United States Patent
Islak et al.

(10) Patent No.: US 10,335,156 B2
(45) Date of Patent: Jul. 2, 2019

(54) SELF-ADAPTING FLOATING DIAMETER EMBOLIC COIL

(71) Applicant: NDI TIP TEKNOLOJILERI ANONIM SIRKETI, Istanbul (TR)

(72) Inventors: Civan Islak, Istanbul (TR); Sadik Semih Demiralp, Istanbul (TR); Garth W. Boyd, Ellington, CT (US); Michael J. Kuske, Waverly, MN (US); Cam E. Habeger, Big Lake, MN (US)

(73) Assignee: NDI TIP TEKNOLOJILERI ANONIM SIRKETI, Istanbul (TR)

( * ) Notice: Subject to any disclaimer, the term of this patent is extended or adjusted under 35 U.S.C. 154(b) by 434 days.

(21) Appl. No.: 15/161,206

(22) Filed: May 21, 2016

(65) Prior Publication Data

US 2017/0020532 A1 Jan. 26, 2017

Related U.S. Application Data

(62) Division of application No. 14/277,022, filed on May 13, 2014, now abandoned.

(51) Int. Cl.
*A61B 17/12* (2006.01)
*A61B 17/00* (2006.01)

(52) U.S. Cl.
CPC .. *A61B 17/12145* (2013.01); *A61B 17/12031* (2013.01); *A61B 17/12109* (2013.01);
(Continued)

(58) Field of Classification Search
CPC .......... A61B 17/1214; A61B 17/12145; A61B 17/1215; A61B 17/12154;
(Continued)

(56) References Cited

U.S. PATENT DOCUMENTS

| 6,635,069 B1 * | 10/2003 | Teoh ................ | A61B 17/12022 606/191 |
| 9,089,405 B1 * | 7/2015 | Gulachenski .... | A61B 17/12113 |
| 2003/0120302 A1 * | 6/2003 | Minck, Jr. ........ | A61B 17/12022 606/200 |
| 2006/0047299 A1 * | 3/2006 | Ferguson ......... | A61B 17/12022 606/200 |
| 2007/0083257 A1 * | 4/2007 | Pal ................... | A61B 17/12022 623/1.22 |

(Continued)

FOREIGN PATENT DOCUMENTS

WO WO-03037191 A1 * 5/2003 ....... A61B 17/12022

*Primary Examiner* — Katrina M Stransky
*Assistant Examiner* — Katherine H Schwiker
(74) *Attorney, Agent, or Firm* — Damian Wasserbauer, Esq.; Damian Wasserbauer

(57) ABSTRACT

An embolic coil configured with a self-adaptive floating diameter in a relaxed condition substantially assuming the shape of the inner surface of the vessel at the site of an embolization procedure. The embolic coil comprises a distal end having an anchoring loop for anchoring at the site, a proximal end with a loop for detaching from a gripper assembly adapted to deliver to the site, a primary framing coil formed of a plurality of primary omega curves extending between the proximate and distal ends, and a secondary filling coil arrangement formed from a plurality of secondary omega curves that follow the trajectory of the plurality of primary omega curves along the longitudinal length of the embolic coil between the proximate and distal ends. The embolic coil conforms to the diameter of the aneurysm sac enabling retractability and rapid disconnect detachment for such embolic coil advantageously requiring fewer embolic coils.

23 Claims, 18 Drawing Sheets

(52) U.S. Cl.
CPC .................. *A61B 17/12113* (2013.01); *A61B 2017/00867* (2013.01); *A61B 2017/1205* (2013.01); *A61B 2017/1209* (2013.01); *A61B 2017/12054* (2013.01); *A61B 2017/12077* (2013.01)

(58) Field of Classification Search
CPC ........ A61B 17/12163; A61B 17/12022; A61B 17/12031; A61B 17/12109; A61B 17/12113; A61B 17/12118; A61B 2017/12054; A61B 2017/1205; A61B 2017/12059; A61B 2017/12063; A61B 2017/12068; A61B 2017/12086; A61B 2017/1209; A61B 2017/12077; A61B 2017/00867; A61B 17/12027; A61B 17/12036; A61B 17/12014; A61B 17/12122; A61B 17/12159; A61B 17/12168; A61B 17/12172; A61B 17/12177; A61B 2017/12072; A61B 2017/12081; A61B 2017/12095

USPC ...................................................... 606/200
See application file for complete search history.

(56) References Cited

U.S. PATENT DOCUMENTS

| | | | | |
|---|---|---|---|---|
| 2008/0082176 A1* | 4/2008 | Slazas | ............... | A61B 17/12113 623/23.72 |
| 2008/0228216 A1* | 9/2008 | Strauss | ............ | A61B 17/12022 606/191 |
| 2012/0041472 A1* | 2/2012 | Tan | .................. | A61B 17/12113 606/200 |
| 2012/0172921 A1* | 7/2012 | Yamanaka | ....... | A61B 17/12022 606/200 |
| 2013/0018409 A1* | 1/2013 | Le | .................... | A61B 17/12109 606/200 |
| 2013/0184743 A1* | 7/2013 | Chen | .................. | A61B 17/1214 606/200 |
| 2015/0289881 A1* | 10/2015 | Suzuki | ............. | A61B 17/12031 72/371 |
| 2015/0297238 A1* | 10/2015 | Ken | ................. | A61B 17/12113 606/200 |

\* cited by examiner

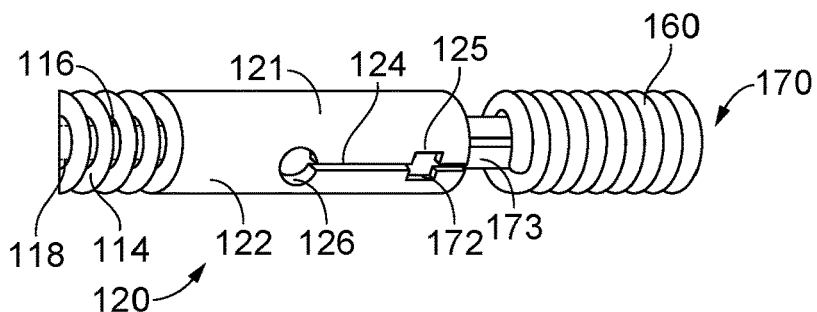
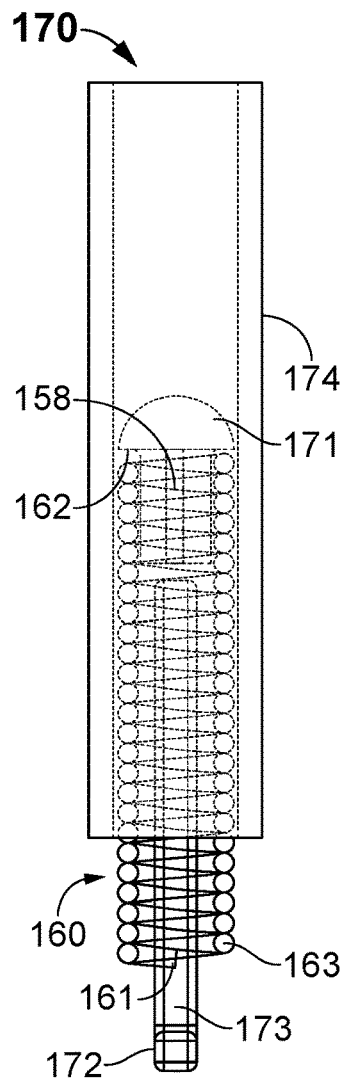 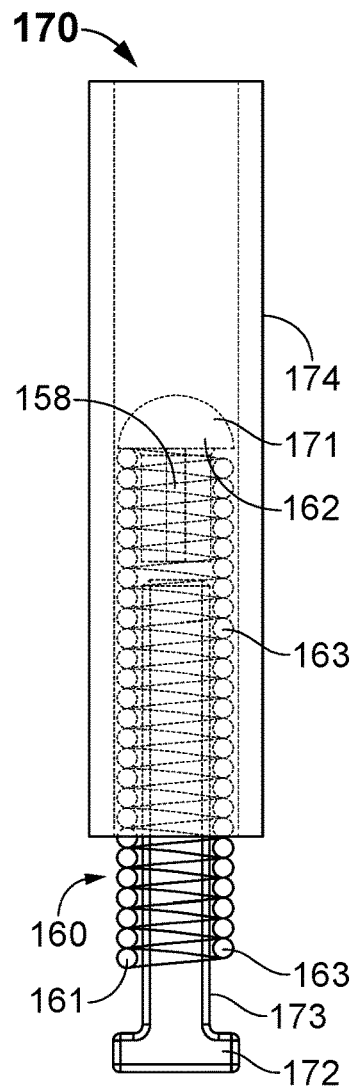
FIG. 1B
FIG. 1C   FIG. 1D

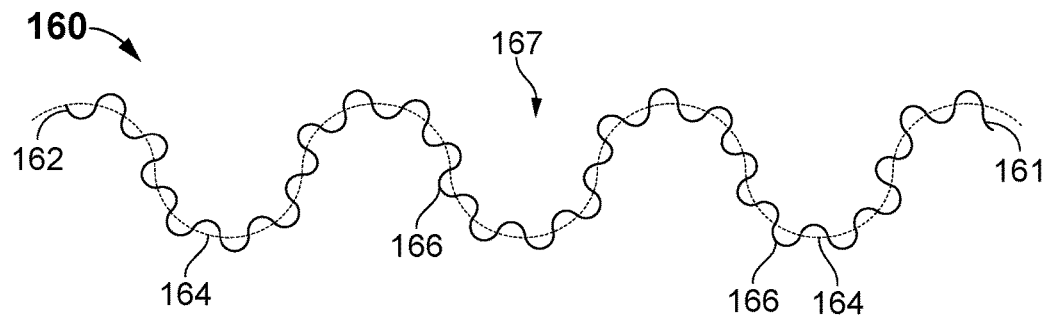
FIG. 13A
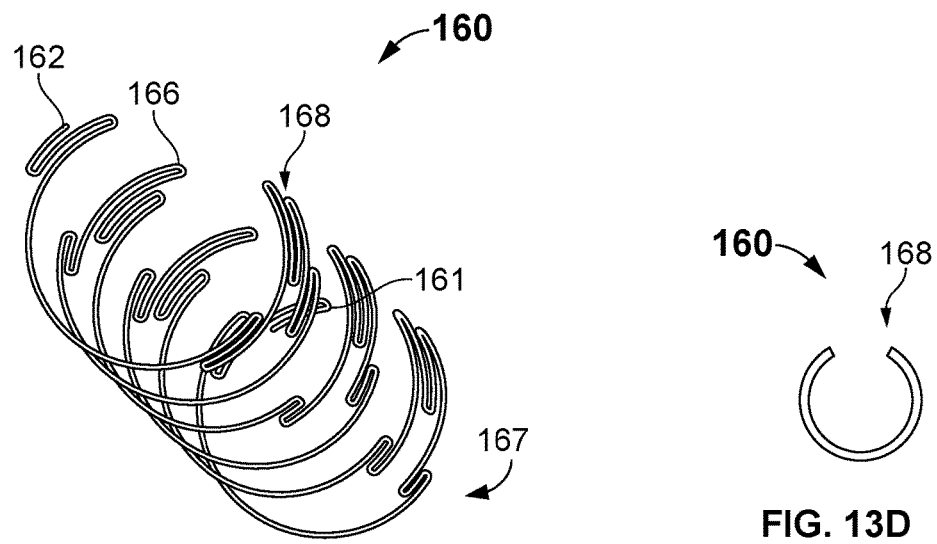
FIG. 13B
FIG. 13D
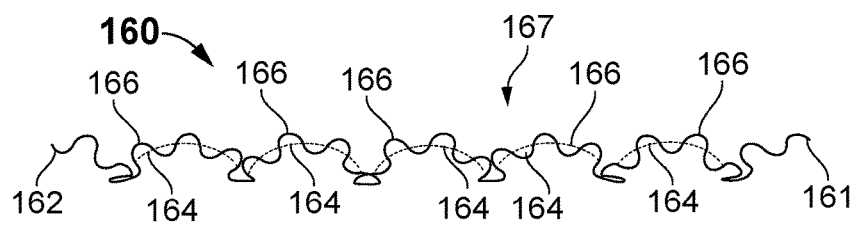
FIG. 13C

SELF-ADAPTING FLOATING DIAMETER EMBOLIC COIL

CROSS-REFERENCE TO RELATED APPLICATION

This application is a divisional of and claims the benefit of U.S. patent application Ser. No. 14/277,022 filed May 13, 2014 entitled "RETRACTABLE AND RAPID DISCONNECT, FLOATING DIAMETEREMBOLIC COIL PRODUCT AND DELIVERY SYSTEM." The patent application identified above is incorporated here by reference in its entirety to provide continuity of disclosure.

FIELD OF THE INVENTION

The present invention relates to an embolic coil product, delivery system, and method for deploying an embolic coil and, more particularly, an embolic coil with specific properties conforming to a diameter of an aneurysm thereby taking the shape of the aneurysm using a method and delivery assembly that can be used to insert, retract, reconnect, and rapidly disconnect from the embolic coil.

BACKGROUND OF THE INVENTION

Conventional mechanical occlusion devices or coils are used for embolization procedures of AVF, aneurysms, or other vascular lesions. These coils can be deployed accurately to a location, e.g. exactly where the catheter ends. In the human brain, different factors such as anatomic anomalies can occur in the arterial blood vessels, thus forming stretched out sacs or aneurysms. Embolization procedures insert coils that may immediately clot the aneurysm sac, thereby stopping the thinner, weaker sidewalls of the arteries from bulging outward from the main lumen.

Conventional primary coils are either simple coil strands or more complex three dimensional scaffolding of varying shapes. Conventional primary or "framing" coils may be formed in complex three dimensional ball-like shapes. Conventional secondary or "filler" coils may be formed in merely simple arc shapes. Coils are made of metal platinum or stainless steel such that coils are easily seen in radiographic images; however, large coils have a disadvantage in that these can disrupt the radiographic image.

Deploying such conventional coils in an embolization procedure involves deploying the framing coil, for example, the diameter in millimeters of the aneurysm sac is typically measured using the imaging system. A particular diameter of the framing coil is selected that is at or less than the dimension of the diameter of the aneurysm sac such that when the primary coil is extruded from the distal tip of the catheter, at body temperature, the framing coil assumes a three dimensional ball shape within the aneurysm sac. Subsequent additional secondary filling coils are inserted in, around and adjacent the scaffold or framing structure established by the primary coil so as to fully fill the aneurysm sac, thereby promoting the clot.

When using conventional embolic coils, multiple coils (e.g., between 10-12) may be needed to fill an aneurysm. For example, "framework" coils and may be used first to line the outer perimeter of the aneurysm, with softer smaller "filler" coils being used to fill the central portion of the cavity. Examples of three dimensional framework coils that function to clot the vessel of the aneurysms for the therapeutic benefit of the patient are disclosed in the following patents: U.S. Pat. No. 8,323,306 B2 to Schaefer et al; U.S. Pat. No. 6,929,654 B2 to Teoh et al.; U.S. Pat. Publication No. 2003/0120302 A1 to Jaeger; and U.S. Patent Publication No. 2013/0018409 A1 to Burke et al.

Conventional framework coils may have problems adapting to the shape and/or diameter of the aneurysm sac because the unfolded predetermined three dimensional shape does not conform to the specific shape of the aneurysm sac, which is different each time as the aneurysm sac forms in all different shapes. Conventional framework coils may form the intended three dimensional shape in an unpredictable fashion and in a less than optimal fit of the aneurysm sac, thereby necessitating multiple coils for an embolization procedure that increase the cost of the embolic procedure.

Conventional three dimensional shapes also are selected at or below the measured diameter of the aneurysm sac, which may result in three dimensional shaped coils not adapting well to the in-between sizes of a measured aneurysm sac. For example, the aneurysm sack is measured at 4.5 mm and the three dimensional shaped coil is only available at a 4 mm dimension. As a result, conventional treatments first secure a 4 mm three dimensional shaped coil in a measured 4.5 mm aneurysm sac by delivering the 4 mm framing coil to line the outer perimeter of the aneurysm, with softer smaller "filler" coils being used to fill the central portion of the cavity. This further results in numerous coils being used (e.g. between 10-12 coils may be needed) to fill an aneurysm sac. In this instance, there is an increased risk of complications to the patient should a coil or part of a coil such as an end, become dislodged or fall out of the sac into the venial cavity.

Conventional coils may also lose shape if they are kinked, such as by the operation of the catheter. Known catheter systems have no way to retract the coil. If an end or kinked end of the coil, or the entire coil dislodges, from the deployed location there is a significant medical risk that the aneurysm may burst or trigger a clot which then causes distal emboli. Such a bleed can be life threatening or such emboli may result in neurologic deficit.

As such, there is a long-felt need in the art to provide an embolic coil with specific properties of conforming to the specific shape of the aneurysm sac, which is different in each embolization procedure, and to uncoil into a predictable, efficient shape, thereby reducing the risk of prolapse of the coil into the parent vessel. There is a need to reduce number of coils required for the embolization procedure so as to overcome disadvantages of the prior art including increases in the procedure time, cost and risk to the patient. A self-adapting floating diameter embolic coil that conforms to the specific shape of the aneurysm sac can have advantages of forming an effective and efficient scaffold structure. An NiTiNOL efficient scaffold structure would result in effective secondary coil filling using other self-adapting floating diameter embolic coils that can reduce drastically embolization procedure time and cost including the number of embolic coils ultimately used.

Another disadvantage of conventional delivery systems embolic coils and methods used in the embolization procedure is that once a coil is positioned, it is necessary to disconnect the embolic coil from the pusher wire. A drawback in the art is that conventional mechanical, electrical and chemical disconnect systems are irreversible disconnects. Improvement in this area would be an advancement in the prior art.

In a conventional mechanical disconnect system, a capture mechanism located on the proximal end of the embolic coil such as, for example, a latch (or trapped ball) captures the embolic coil for pushing/pulling with a secondary wire or cable that extends down the length of the lumen of the catheter, whereby pulling on the cable opens and release the embolic coil from the latch. Mechanical disconnect systems may perform relatively rapidly; however, this required mechanical movement to disconnect has disadvantages as any mechanical movement to free the embolic coil can cause undesirable movement of the placement of the embolic coil such as, for example, leaving a tail of the embolic coil hanging in the lumen of the artery where it can cause turbulence, and other adverse events. Another disadvantage of conventional mechanical disconnect connections is that once released from the latch, the embolic coil is free and no more control can be exerted over the coil.

In a conventional electrical disconnect connection system, a fusible link is used to disconnect the capture mechanism from the proximal end of the coil. In such systems, an electric current is applied to the pusher wire, whereby the current heats and melts a short portion of the pusher wire proximal to the coil. Electrical disconnects generally use a battery and some sort of push button to connect a circuit that includes the battery, the pusher-wire, a fusible link, and in some embodiments a return wire. Other times the return path of the electrical current flows through the patient's body to a body surface reference electrode. Similarly, electrical disconnect connections have disadvantages of coil control, whereby no more control can be exerted on the embolic coil once released and free of the pusher-wire of the catheter. Similarly, in conventional chemical disconnect connection systems a fusible link is used that is chemically releasable so as to disconnect the capture mechanism from the proximal end of the coil.

As discussed, known catheter systems have no way to retract and/or recapture the coil. If an end of the coil, or the entire coil, dislodges from the deployed location, there is a significant medical risk that the aneurysm may rip or burst, which can be life threatening. As such, there is a long-felt need in the art to provide an embolic coil and delivery system and method of treatment that can recapture and, therefore, control an embolic coil. There also is a related need to reduce embolization procedure time, cost including the number of embolic coils used, and health risks.

SUMMARY OF THE INVENTION

It is an object of the present invention to provide an assembly, system and method for delivering a vaso-occlusive device or embolic coil with the delivery assembly configured with a gripper assembly with a jaw configured to open and close for delivering the embolic coil to the site of the embolization procedures. The gripper assembly is configured to re-connect the jaw of the gripper assembly to the embolic coil by opening and closing the jaw on a loop of the embolic coil, preferably a proximal loop. The gripper assembly can be actuated to release the embolic coil with no mechanical force being applied by the gripper assembly to disconnect from the embolic coil.

It is an object of the present invention to provide a vaso-occlusive device, and/or an embolic coil with a predetermined shape along its length that the embolic coil has specific properties conforming to a diameter of an aneurysm thereby taking the shape of the aneurysm in a relaxed condition with improved efficiency. The embolic coil can use the delivery assembly and method for delivering the embolic coil to insert, retract, reconnect, and rapidly disconnect the embolic coil from the delivery system in an embolization procedure.

It is an object of the present invention to provide a method of occluding a selected site in a vessel with a vaso-occlusive device, the method has the steps of accessing the site with a delivery assembly; deploying the vaso-occlusive device from the delivery assembly into the selected site of the vessel in a manner allowing the vaso-occlusive device to substantially assumes a shape of an inner surface of the vessel at the site; and, if required, connecting said delivery assembly to a proximal end of the vaso-occlusive device in the vessel in during an embolization procedure.

It is an object of the present invention to provide an gripper assembly for delivering a vaso-occlusive device or embolic coil to a location in a patient's vasculature, with an improved a gripper assembly a jaw configured to open and close on a proximal portion of the embolic coil. The delivery assembly is configured with a core wire disposed in an intermediate spring coil of a delivery tube, with the core wire and a ground wire being electrically coupled to the gripper assembly and disposed in said intermediate spring coil of said delivery tube, and the jaw of the gripper assembly can be energized to move between the open and closed position by applying a positive bias electrical contact to a proximal end of the core wire and a proximal end of said ground wire to said gripper assembly, whereby an electrical circuit is formed so that by energizing said electrical contact said jaw moves to an open position.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Description of the Embodiments, which is to be read in association with the accompanying drawings, which are incorporated in and constitute a part of this specification, show certain aspects of the subject matter disclosed herein and, together with the description, help explain some of the principles associated with the disclosed implementations, wherein:

FIGS. 1A, 1B taken along lines A-A of FIGS. 1A, 1C and 1D illustrate schematic views of a coil in the delivery system in accordance with an embodiment of the present invention;

FIGS. 13A, 13B, 13C and 13D illustrate schematic side views of tertiary arrangements in accordance with an alternative embodiment of the present invention;

DESCRIPTION OF THE EMBODIMENTS

Figure 1A:
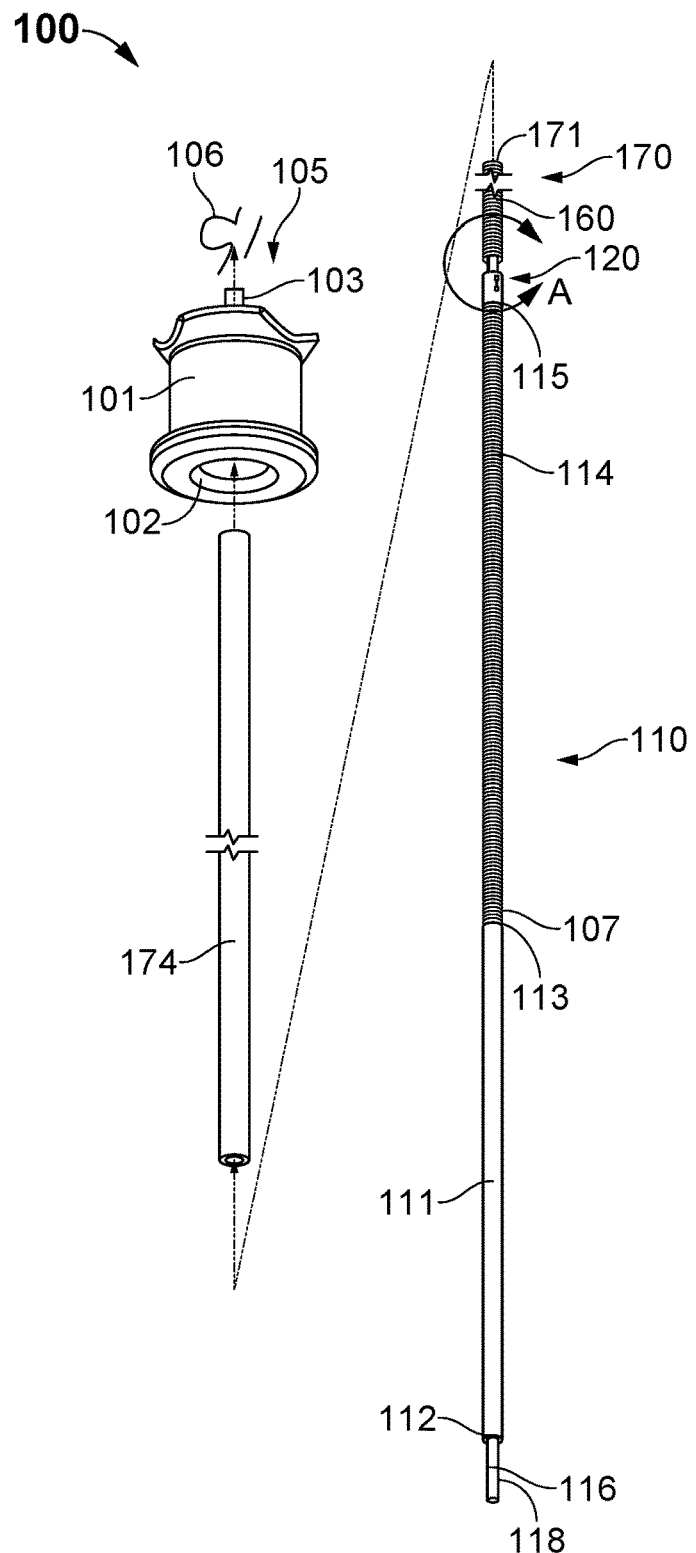

Non-limiting embodiments of the present invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein the term "aneurysm", "intracranial aneurysm", "brain aneurysm" or "cerebral aneurysm" refers to a cerebrovascular disorder where a bulge or that develops in an artery because of weakness in the wall of a cerebral artery or vein, thereby causing a localized dilation or ballooning of the blood vessel. In the brain, a bulging aneurysm can compress surrounding nerves and brain tissue resulting in nerve paralysis, headache, neck and upper back pain as well as nausea and vomiting. If an aneurysm in the brain ruptures, causing an opening in the wall, the resulting bleeding in the head may cause a stroke or death.

As used herein the term "arteriovenous malformation" or "AVM" refers to an arteriovenous malformation that is an abnormal connection or passageway between the arteries and veins. AVMs may prevent oxygenated blood from completely circulating throughout the brain, causing symptoms including, but not limited to: unusual sound in one ear such as pulsating or humming neurological symptoms' increased pressure in the eye such as glaucoma; double vision; and pain.

As used herein the term "catheter" or "micro catheter" refers to a medical device formed as a flexible, tubular instrument allowing to be passed into a blood vessel or patient's body cavity and used to withdraw fluids, inject medicine or contrast materials. Conventional dimensions are a long, thin plastic tube approximately ⅛ inch in diameter. In an embolization procedure, a catheter typically is passed through the abdomen into the system of branching blood vessels to the site of the aneurysm and/or embolism.

As used herein the term "coil" or "embolic coil" refers to a vaso-occlusive device defined by a micro-coil having an initial configuration in which the device may be delivered to vasculature and a secondary configuration where the device takes another form where it may be used for occluding an aneurysm. The micro-coil may be formed with primary and secondary curves, also referred to as primary omega and secondary omega, for base or framing coils, and for filling coils.

As used herein the term "CT X-Ray", "CT scan" or "CAT scan" refers to X-ray Computed Tomography technology that uses computer-processed x-rays to produce tomographic images (virtual 'slices') of specific areas of the scanned object, allowing the user to see what is inside it without cutting it open. CAT scan equipment and methods use digital geometry processing to generate a three-dimensional image of the inside of an object from a large series of two-dimensional radiographic images taken around a single axis of rotation. According to embodiments of the present invention, CAT scan equipment and methods are used in medical imaging as cross-sectional images are used for diagnostic and therapeutic purposes in various medical disciplines As used herein the term "delivery system" "delivery apparatus" or "delivery device" refers to a micro catheter configured to deliver embolic coils and other things to the site of an aneurysms, arteriovenous malformations embolism, embolization or other vascular lesions such as in an embolization procedure.

As used herein the term "embolization" refers to a non-surgical, minimally invasive procedure performed by interventional radiologists and interventional neuroradiologists involving the selective occlusion of blood vessels by purposely introducing emboli so as to deliberately block a blood vessel. Embolization of brain aneurysms and arteriovenous malformations (AVM)/fistulas is a minimally invasive treatment for aneurysms and other blood vessel malformations that occur in the brain. These problems are typically identified in adults; however, aneurysms and AVMs can also occur in children.

As used herein the term "embolization procedure" refers to a procedure where a radiologist, surgeon or other physician uses image guidance to place small, soft metal coils within the aneurysm, whereby the embolic coil helps block the flow of blood and prevents rupture of the aneurysm. Similarly, procedures for arteriovenous malformation use image guidance and can fill the arteriovenous malformation with a coil provided that the arteriovenous malformation contains direct arteriovenous fistula(e). Similarly, surgical procedures for vascular lesions use image guidance and can fill vascular lesion with a coil.

As used herein the term "intervention" or "interventionist" "interventional radiologist" and/or "interventional neuroradiologist" refers to a sub-specialty of radiologist, physician, and/or surgeon that undertakes actual intervening procedures to institute therapy, or to accomplish diagnosis, and/or uses minimally-invasive image-guided procedures to diagnose and treat diseases in nearly every organ system.

As used herein the term "MRI" or "NMR" refers to Nuclear Magnetic Resonance Imaging uses a physical phenomenon where nuclei placed in a magnetic field absorb and re-emit electromagnetic radiation for medical diagnosis. NMR is also routinely used in advanced medical imaging techniques, such as in magnetic resonance imaging (MRI).

As used herein the term "sac" or "sack" refers to a hollow, flexible structure resembling a bag or pouch and, in particular, in the patient's body, a cavity enclosed by a membrane, distended membrane or vascular tissue.

As used herein the term "self-adaptive floating diameter" refers to a function of the coiling shape wanting to float to the diameter of the aneurysm sac.

As used herein the term "shape-memory alloy" or "NiTi" or "NiTiNOL" refers to any metal alloy or polymer that when heated or warmed takes the heat treated shape and when cooled takes another shape. Metal alloys such as titanium (Ti) and nickel (Ni) commonly called NiTiNOL is a memory metal in that when heated or warmed the metal takes the heat treated shape and when the metal cools the metal takes another shape. Suitable shape-memory alloys include a biocompatible metal wire, NiTi, platinum, tungsten, titanium, gold, iridium, palladium, tantalum, stainless steel or a platinum alloy. As used herein the term "shape-settable alloys" refers to any metal alloy or polymer that when heated or receives heat-treatment takes the heat treated shape. Shape-settable alloys include a biocompatible metal wire, platinum, tungsten, titanium, gold, iridium, palladium, tantalum, or a platinum alloy.

As used herein the term "vaso-occlusive device" refers to an embolic coil or a micro-coil having an initial configuration in which the device may be delivered to vasculature and a secondary configuration where the device takes the form of a cylindrical-shaped device defining an elongated c-shape where it may be used for occluding an aneurysm. The micro-coil is formed of a primary coil or base coil. Generally, the base coil is a straight wire wound to form coils of a diameter of various sizes.

Figure 15A:
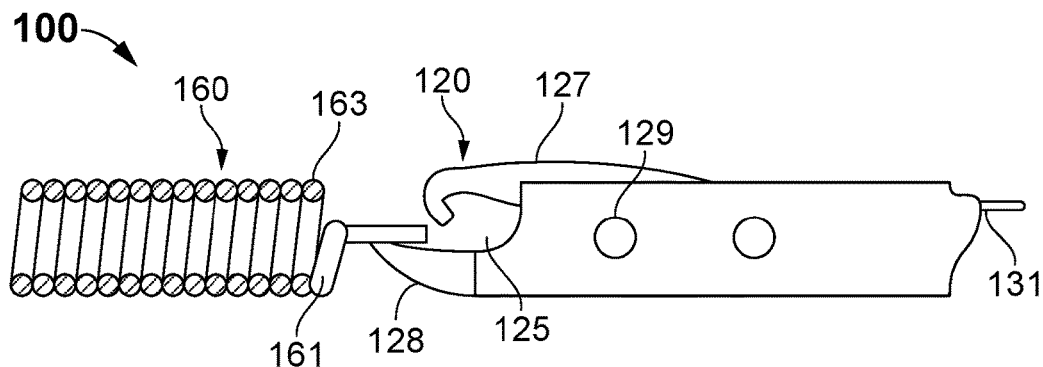
FIGS. 15A and 15B illustrate schematic views of open and closed positions of a mechanical gripper assembly in accordance with an embodiment of the present invention.
Figure 15B:
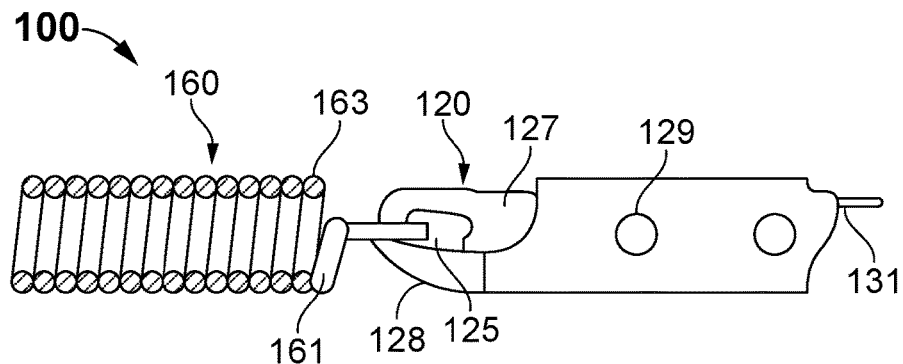

Referring now to FIGS. 1-21, a medical therapeutic embolic device, system and method for an embolization procedure is described and generally referred to by reference element 100. As illustrated in FIGS. 1A-1D, 2 and 3, the system 100 is configured to use with a loading sheath 174 to insert in a micro-catheter 101 (e.g. FIGS. 1, 19A and 20A) having a general elongated tubular shape with an open proximal end 102 and a distal end 103. The system 100 comprises a delivery assembly 110 configured with a gripper assembly 120 to hold a coil assembly 170 so as to deploy an embolic coil 160 to a site of an aneurysm 105 (e.g. FIGS. 1 and 19A) and release the embolic coil 160 into a sac 106 of the aneurysm according to embodiments of the present invention. The gripper assembly 120 can be formed in various alternative embodiments for gripping the embolic coil 160, for example, a mechanical gripper as shown in FIGS. 15A and 15B, a mechanical gripper with electrical assist, as shown by the jaw assembly in FIGS. 17A, 17B, 18A and 18B, as well as the mechanical jaw FIGS. 15A and 15B in combination with electrical assist from the shape-memory alloy wire of FIGS. 16A and 16B, or a balloon gripper assembly 120 as is shown in FIGS. 21A, 21B, 21C and 21D.

Referring to FIGS. 1A, 1B, 4 and 5A, the delivery assembly 110 comprises a delivery tube 111 with a proximal tube portion 112 and a distal tube portion 113, intermediate coil 114 with a proximal coil end 107 and a distal coil end 115, a core wire 116, and a ground wire 118, with each of the core and ground wires 116, 118, respectively, connecting to a distal tip 119 secured to the gripper assembly 120. The delivery tube 111 can be formed from a suitable material such as NiTiNOL or NiTi. A proximal coil portion 107 of the intermediate coil 114 can be connected to the distal tube portion 113 by suitable means such as adhesives and the like. The intermediate coil 114 formed as a flexible spring to provide maneuverability to the gripper assembly 120 and made from a suitable material (e.g. stainless steel) which is flexible, resilient and withstand conditions of use in the patient's body including the brain with later sterilization for reuse. The distal tip 119 can be formed from silver filled epoxy. The delivery assembly 110 is configured to accept and deliver, and to advantageously re-attach, if necessary, the embolic coil 160 to the sac 106 of the aneurysm for the embolization procedure.

As illustrated in FIGS. 1A-1D, 4 and 5A, the coil assembly 170 includes the embolic coil 160, which may be formed from of a metallic or polymer composition. In the embolization procedure, one or more embolic coils 160 serve as a stabilizing structure or scaffold causing blood to coagulate and form thrombus which fills the aneurysm cavity, thereby preventing the rupture of the aneurysm and subsequent bleeding. As shown in FIGS. 1A, 1B, 1C and 1D, an embolic coil 160 having multiple loops of a primary winding 163 can be configured in a coil assembly 170 that can be deployed by the delivery assembly 110 in accordance with an embodiment of the present invention. The coil assembly 170 comprises the embolic coil 160 in combination with a tip 171 at a distal end of the coil 162, and a T-pin 172 with a stem portion 173 connected to a proximal end of the coil 161. A stretch resistant filament 158 is configured to maintain the shape of the distal end of the coil 162 in the coil assembly 170 and is useful for handling and transportation, as is shown in FIGS. 1C and 1D. It should be understood that FIGS. 1B, 1C and 1D show the coil assembly 170 at a stage where it is being initially inserted into the catheter 101, and that the coil assembly 170 will be advanced distally through the catheter 101 to allow additional components to be positioned in the catheter 101 proximal to the coil assembly 170 as shown in FIGS. 1A-1D, 4 and 5A. It should also be understood that FIGS. 1C and 1D only show a proximal portion of sheath 174 that is inserted in the catheter 101.

Figure 2:
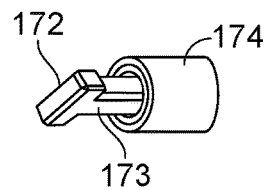
FIG. 2 illustrates a schematic view of a T-Bar of the proximal end of the embolic coil assembly in accordance with an embodiment of the present invention.
Figure 3:
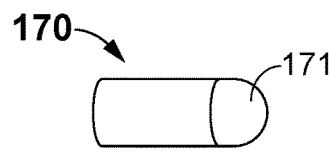
FIG. 3 illustrates a schematic view of a distal end and sheath of the embolic coil assembly in accordance with an embodiment of the present invention.
Figure 5A:
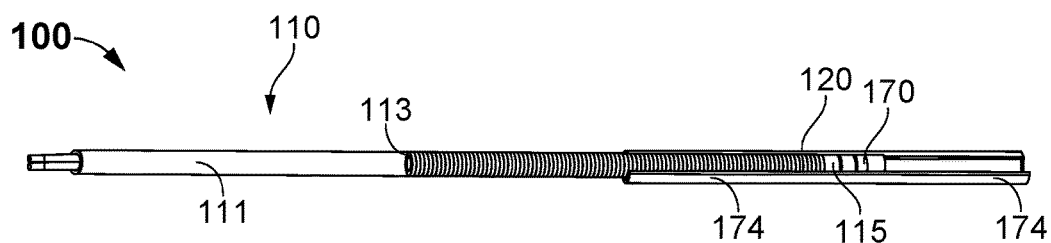
FIGS. 5A and 5B illustrates a schematic exploded view of a delivery assembly and coil assembly in the catheter in accordance with an embodiment of the present invention.

FIG. 2 illustrates a schematic view of a proximal end of the embolic coil 160 in accordance with an embodiment of the present invention. As shown in FIG. 2, the T-pin 172 is shown being inserted into a proximal end of a portion of the sheath 174, which is advanced to the distal end of the sheath 174, as shown in FIG. 5A. The T-pin or bit 172 can protrude from the end so that the gripper assembly 120 can attach thereto. As shown in FIG. 3, the rounded coil assembly tip 171 can be made of suitable materials such as a metal alloy or polymer. As shown in FIGS. 1A, 1C, 1D and 3, the sheath 174 may be used and is useful to assist in loading the coil assembly 170 into the proximal end 102 of the catheter 101, and to keep the coil 160 protected for shipping the coil assembly 170. The sheath 174 is removed prior to use of the catheter 101 and delivery assembly 110 in the patient's body. The embolic coil assembly 170 can be inserted into the proximal end 102 of the catheter 101 of the delivery assembly 110, as illustrated in FIG. 1A. The delivery assembly 110 can push the embolic coil assembly 170 end to end, from the proximal end 102 to the distal end 103 of the catheter 101, to the site of the aneurysm 105, as is shown in FIGS. 1A, 2, 5A, and FIGS. 19A-19C.

As shown in FIG. 1B, the coil assembly 170 is attached to a tip 121 of the gripper assembly 120 to the delivery assembly 110. The embolic coil 160, as arranged on the stem 173 in the assembly 170, is held by the T-pin 172 in the recess 125 of the jaw 122 of the gripper assembly 120. The jaw 122 of tip 121 opens along opening 124 to an open position using hinge 126 to receive the T-pin 172 by actuating with the electrical energy transmitted to the tip 121 by a core wire 116 and a ground wire 118 disposed within the intermediate coil 114. The jaw 122 of tip 121 closes around the T-pin 172 by halting energy, whereby the tip 121 moves to a closed position securing the embolic coil 160 and/or coil assembly 170 thereto. The coil assembly 170 is configured with a suitable dimension to deliver one or more embolic coil(s) 160 to the site 105 of an aneurysms, arteriovenous malformations embolism, or other vascular lesions such as in an embolization procedure.

Referring to FIGS. 1A-1D, 4, 5A, and 19A-19C, once the proximal end 161 of the embolic coil 160 is attached to the tip 121, for example, via a T-pin or bit 172, which is selectively grasped by the gripper assembly 120 as described in greater detail herein, it can be deployed to the sac 106 of the aneurysm for the embolization procedure. In some versions that lack the T-pin or bit 172, the proximal end 161 of the embolic coil 160 is bent to form a loop that is orthogonally oriented in relation to the rest of the loop 163 of the embolic coil 160. An example of such an orthogonally looped proximal end 161 is shown in FIGS. 15A-15B and is described in greater detail below as the gripper assembly 120 is configured to grip any part of the embolic coil 160.

Figure 19A:
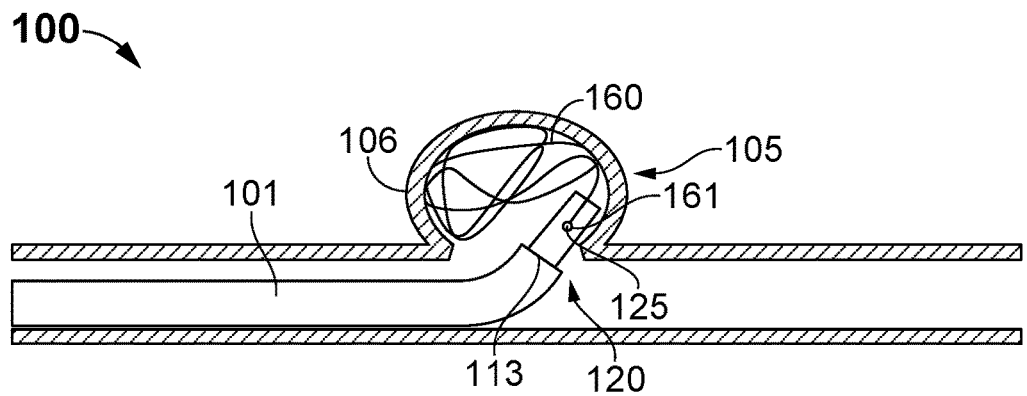
FIGS. 19A, 19B, and 19C illustrate schematic views of using a delivery system in an embolization procedure deploying an embolic coil into the sac in accordance with an embodiment of the present invention.
Figure 19B:
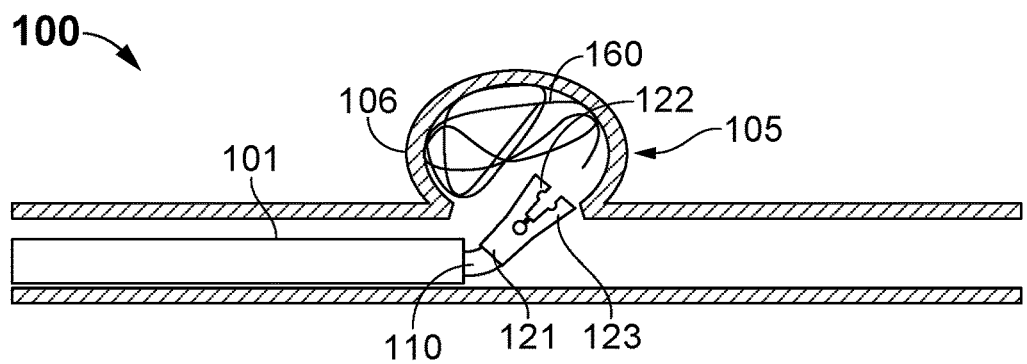
Figure 19C:
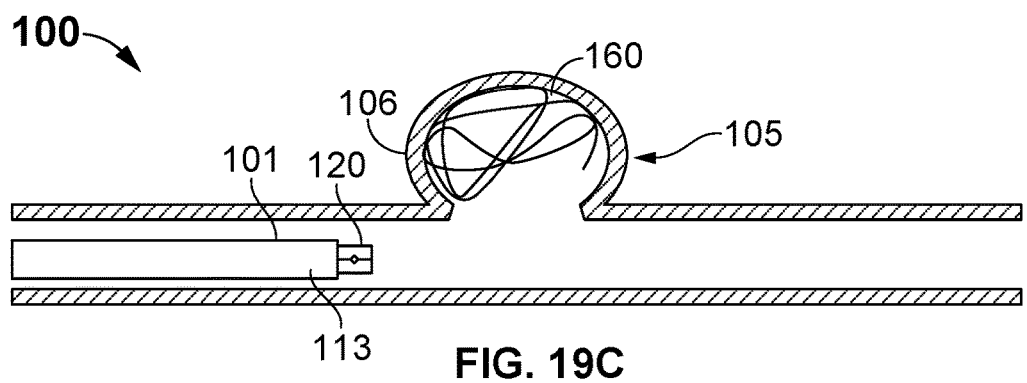

The distal end 103 of the catheter 101 is maneuvered to the opening of the aneurysm 105, which may be referred to as the neck, as illustrated in FIG. 19A. The embolic coil 160 is advanced along the catheter 101 and deployed into the aneurysm utilizing the micro catheter by pushing to the site of the embolization procedure, as illustrated in FIGS. 1A and 19B. The embolic coil 160 is allowed to coil up in the aneurysm until the sac 106 is adequately filled. The embolic coil 160 can then be detached and left behind as illustrated in FIG. 19C. In operation, the embolic coil 160 is inserted into a proximal end 102 of the catheter 101, as shown in FIG. 1A. The embolic coil 160 is secured by the gripper assembly 120 at one end, with the embolic coil 160 still inserted in sheath 174. The sheath 174 can be removed as the delivery assembly 110 is pushed along the catheter 101 out of the distal end 103 of the catheter 101. The embolic coil 160 is thereby pushed into the aneurysm sac 106 where it coils, as shown in FIGS. 19A and 19B, and then the delivery assembly 110 is retracted from the site, as shown in FIG. 19C.

Figure 4:
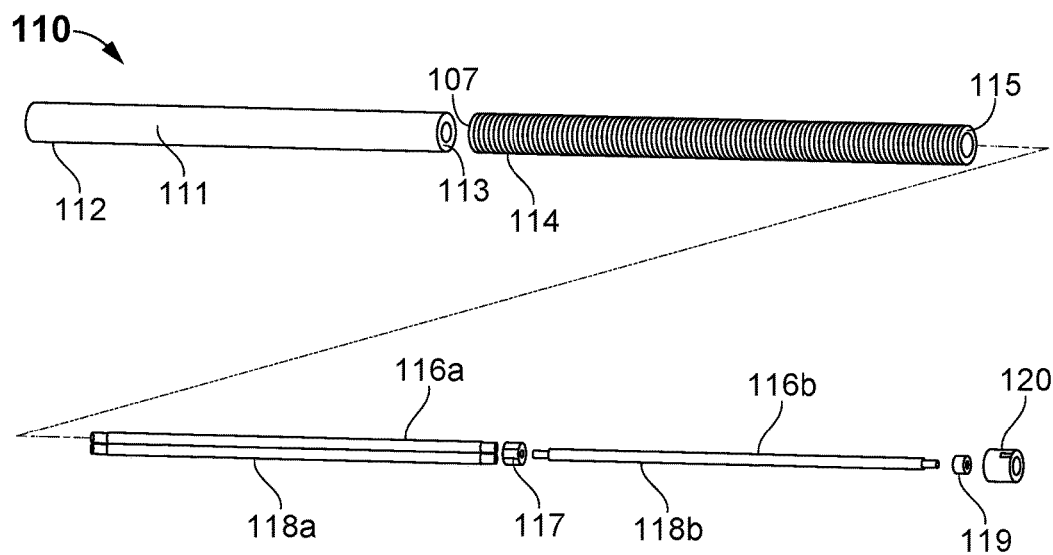
FIG. 4 illustrates a schematic exploded view of a delivery assembly.

Referring to FIGS. 1, 4, and 5A, the delivery assembly 110 is configured with a delivery tube 111 that can be made in hollow, tubular shape from suitable materials, for example, a NiTiNOL tube. The delivery tube 111 is connected to a intermediate coil 114 that may be formed from, for example, platinum wire (a platinum coil of 0.014 OD, wire of 0.0025 and pitch of 0.004) or other suitable materials such as shape-memory alloys as is discussed herein with reference to FIGS. 15A-18B. The wire of the intermediate coil 114 forming the distal coil portion 115 can be wrapped in a tight helix about the longitudinal axis to be resilient in operation as well as configured to be affixed at the tip 121 of the gripper assembly 120. The proximal coil portion 107 of the intermediate coil 114 may be bonded to the distal tube portion 113 of the delivery tube 111 in an end-to-end arrangement.

Referring to FIG. 4, the delivery assembly 110 is configured with one or more wires of differing dimensions forming a taper from end to end in order to form an electrical circuit for operating the gripper assembly 120. As above, the core wire 116 and ground wire 118 may be formed from suitable wire and cable, for example, coax cable, twisted pair, etc. The core wire 116 and the ground wire 118 are coaxially disposed inside the tube 111 and coil 114 terminating in the electrically conductive base of tip connector 119 of tip 121. The tip connector 119 can be formed from silver-filled epoxy configured to conduct thermal properties from the excitation of the electricity the NiTiNOL material of the gripper assembly 120 so as to actuate jaw 122, or jaws 122, 123, according to exemplary embodiments of the present invention In an alternative embodiment, as is illustrated in FIG. 4, the core and ground wires 116 and 118, respectively, can be configured to change from a large dimension wire to smaller dimension wire along the length of the delivery assembly 110 as the smaller dimensions are useful at the site of the sac 106. For example, core wire 116a of one dimension is connected by a connector 117 to core wire 116b of another dimension so as to taper and terminate at the tip connector 119. Similarly, ground wire 118a of one dimension is connected by a connector 117 to ground wire 118b of another dimension so as to taper and terminate at the tip 119. The wires 116 and 118 can be formed from suitable materials such as, for example, different dimensioned magnet wire and advantageously coated with an insulative coating, for example, 40 and 45 Magnetic wire Heavy Polyurethane 180, respectively, and manufactured from MWS Wire industries. Connector 117 is configured to securely connect wires 116 and 118 together, and may be formed of electrically thermo conductive material to conduct current to the tip connector 119. The connector 117 can be a suitable electrical connector with insulative properties such as conductive metals and insulative coatings or shrink tubing.

Figure 17A:
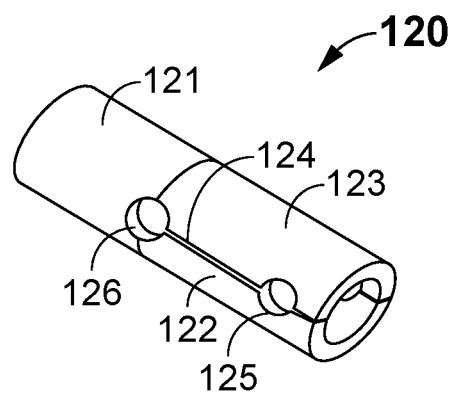
FIGS. 17A and 17B illustrate schematic views of a two-way jaw movement of a gripper assembly in accordance with an embodiment of the present invention.
Figure 17B:
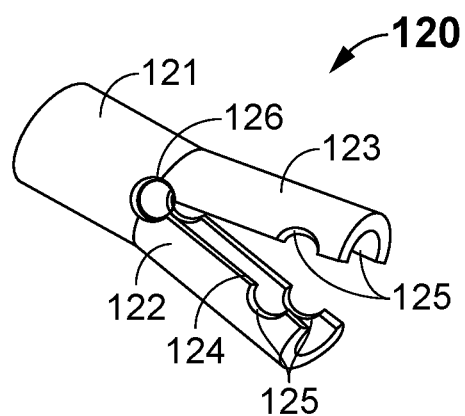
Figure 18A:
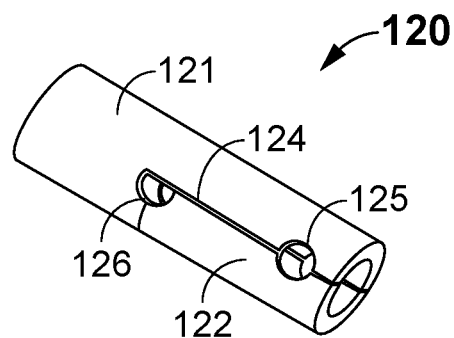
FIGS. 18A and 18B illustrate schematic views of a one-way jaw movement of a gripper assembly in accordance with an alternative embodiment of the present invention.
Figure 18B:
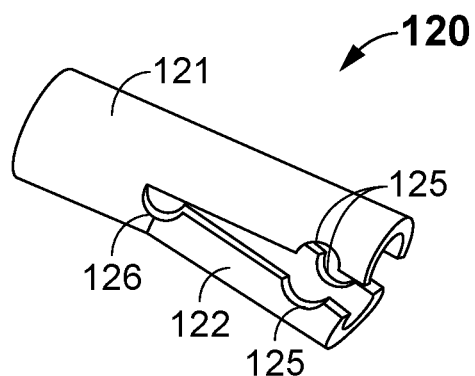

An electrical circuit is formed to operate the gripping assembly 120 using the core wire 116 and the ground wire 118. For example, the electrical circuit can be a DC voltage applied in positive (+) bias having a conductive path formed from the core wire 116 to the distal connector tip 119 and from the distal connector tip 119 returning via the ground wire 118. In operation, when an electrical contact selectively connects the core wire 116 to a source of electricity, such as by a switch, the electrical contact is coupled to the tip connector 119, thereby warming or otherwise heating it via the silver-filled epoxy material composition configured to conduct thermal properties from the excitation of the electricity transferred from wire(s) 116a, 116b, 118a, 118b to the NiTiNOL material of the gripper assembly 120. As is illustrated in FIGS. 17A and 17B, as the NiTiNOL material warms connector tip 119 transmitting heat to the tip 121 of gripper assembly 120, thereby opening more than one jaws (e.g. 2, 3, 4 . . . n jaws), the lower jaw 122 and upper jaw 123 pivot open at hinge 126 to an open position. Similarly, in a single jaw 122 gripper assembly 120, as the NiTiNOL material warms tip 119, lower jaw 122 pivots open at hinge 126 to the open position, as such progression as is shown in FIGS. 18A and 18B. In this manner, the delivery assembly 110 can operate the gripper assembly 120 at a distal location of the site 105 of the aneurysm sac 106 between the open and closed positions so as to hold securely an orthogonally looped proximal end 161 of the embolic coil 160, release the orthogonally looped proximal end 161 with no force on the embolic coil 160 into the aneurysm sac 106, and/or to re-connect to the embolic coil 160, as needed, which is an improvement over the prior art.

Referring to FIGS. 1B, 4, 17A through 18B, the tip 121 operates to move to an open and closed position when it warms and cools. The tip 121 is formed from shape memory alloys such as a NiTiNOL material. The core wire 116 and ground wire 118 terminate in the tip connector 119. The tip connector 119 may be formed from electrically-, thermally-conductive material (e.g. silver filled epoxy) so as to open and close the jaw(s) 122, 123 by applying and removing heat or current to any wire(s) 116, 118. The tip connector 119 is adapted to securely fit into, hold and operate the gripper assembly 120. In an alternative embodiment, the tip 121 is warmed and cooled via the core wires 116a and 116b and the ground wires 118a and 118b are connected via connector 117 and disposed within the loops of the intermediate coil 114 so as to deploy the embolic coil 160 to the site 105.

Figure 6A:
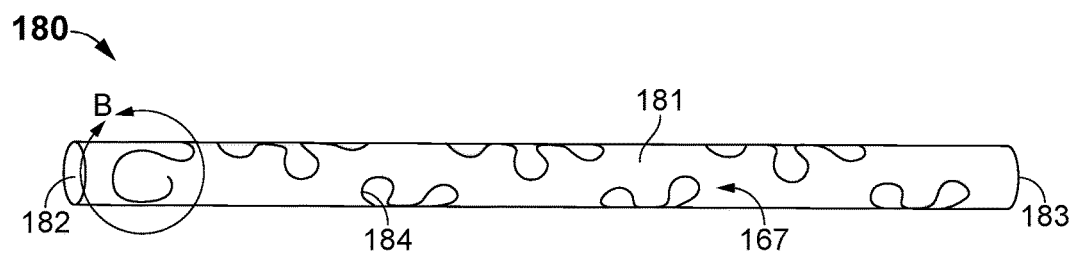
FIGS. 6A and 6B, taken along lines B-B of FIG. 7A, are a perspective views of a mandrel utilized to fabricate a coil according to an embodiment of the present invention.
Figure 6B:
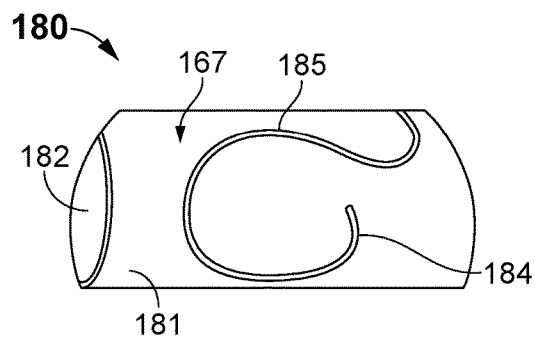

As illustrated in FIGS. 6A through 13D, the embolic coil 160 of the present invention can be made on a mandrel 180 from a metallic or polymer composition including various raw materials that are biocompatible, such as metal wires and resins, but particularly preferable is use of a shape-memory metal wire which is stable in its shape and, in particular, can form a helically wound embolic coil. Examples of materials for the biocompatible metal wire include NiTi, platinum, tungsten, titanium, gold, iridium, palladium, tantalum, and the alloys thereof, stainless steel and the like and, in particular, a metal wire of platinum or a platinum alloy is preferable. As shown in FIGS. 6A and 6B, the mandrel 180 is configured in a generally cylindrical shape with a surface 181 and ends 182, 183. The mandrel 180 is also configured with a tool path 184 having an edge 185 for ease of manufacture by an end mill (not shown), whereby the end mill follows perpendicularly edge 185 and tool path 184 of the predetermined shape 167 so as to form the coil 160. The mandrel 180 can be manufactured from suitable material such as, for example, such as magnetic steel that can withstand the high temperatures of heat treatment, e.g. above 400 degrees Fahrenheit, as is know in the art. The mandrel 180 can be formed in the ordinal plane the predetermined shape 167 of the embolic coil 160 follows a path about a circular, cylindrical, conical, oscillating, spherical or triangular form along its longitudinal axis. an arrangement of waveform-like curves extending along a length of the device between a proximal end and a distal end, as is described herein with reference to FIGS. 14A through 14I, Referring generally to FIGS. 7 through 13D, and specifically to FIGS. 11A-11C, the embolic coil 160 has a proximal end 161 and distal end 162 and folds into an end-to-end length of primary winding 163. As shown in FIGS. 15A and 15B, some versions of the embolic coil 160 include an orthogonally looped proximal end 161. The embolic coil 160 can have a predetermined shape 167 configuring as a primary coil 164, secondary coil 166, a tertiary 168 and an ordinal 169 arrangement. While the embolic coil 160 has sufficient flexibility to be packed into a catheter 101, the embolic coil 160 is resiliently biased to assume the shape of the predetermined shape 167 as soon as the embolic coil 160 is released from the confines of the catheter 101.

Figure 5B:
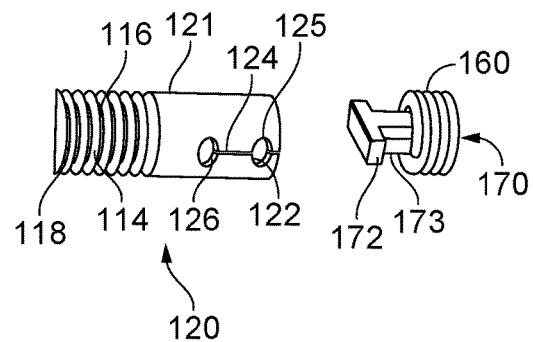
Figure 7:
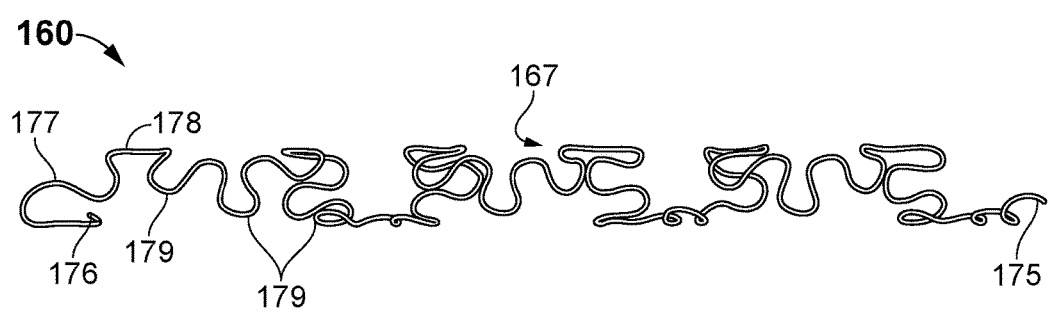
FIG. 7 illustrates a perspective top view of a coil in accordance with an embodiment of the present invention.
Figure 8:
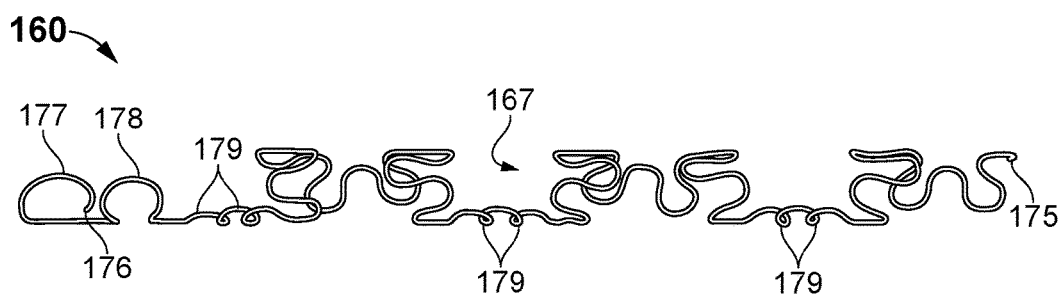
FIG. 8 illustrates a perspective side view of a coil.
Figure 10:
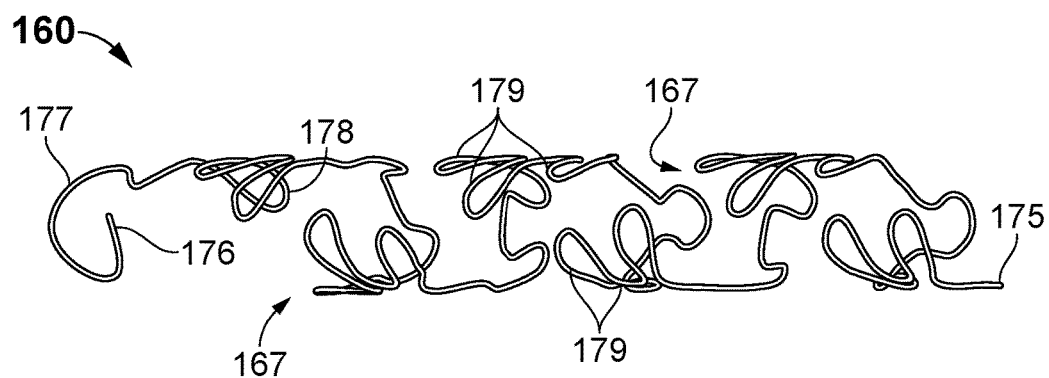
FIG. 10 illustrates a perspective top view of a coil in accordance with an alternative embodiment of the present invention.

As illustrated in FIGS. 1A-1D, 2, 3 and 5A, the coil assembly 170 includes a rounded tip 171 configured to be at a distal end of the assembly 170 so as to assist movement and insertion into the site without additional trauma. For insertion, as shown in FIG. 5B, the tip 121 is arranged adjacent the T-pin 172 of the coil assembly 170 so as to be able to grasp in recess 125 of opening 124 of jaw 122. FIGS. 1C, 1D and 3, illustrate views of a distal end 162 of the embolic coil 160 in accordance with an embodiment of the present invention. The rounded tip 171 or head of a generally rounded shape is formed in the coil as a distal tip, for example, in a distal region of the embolic coil 160. The rounded tip 171 can also be made from the metals and resins described herein such as platinum or NiTi. The rounded tip 171 is configured to be at a distal end 162 of the embolic coil assembly 170 so as to assist movement and insertion into the site without additional trauma. The surfaces and ends of the T-pin 172 are electro-polished Titanium that removes a portion of its mass and rounds the edges to insert into the site without additional trauma. The tip 171 can be securely attached to, for example, the distal end or G-loop end 176 of an elongated, un-coiled state of the embolic coil 160, as shown in FIGS. 7, 8 and 10.

The T-pin 172 is formed with a stem portion 173 configured to be held by the gripper assembly 120 and pushed by the delivery assembly 110 to the site of the aneurysm 105. The surfaces and ends of the stem portion 173 are electro-polished to prevent tissue trauma at the site 105. The stem portion 173 is attached to curled proximal end 175 of the embolic coil 160, as shown in FIGS. 7, 8, 9 and 10. The T-pin 172 and stem portion 173 may be disposed orthogonal to the plane of movement along the catheter 101, as is illustrated in FIGS. 1A-1C, 2, and 5A, or alternatively, a proximal coil end 161 and/or proximal end 175 of sufficient orthogonality, whereby these structures of the embolic coil 160 and coil assembly 170 are configured to be held by the gripper assembly 120, pushed by the delivery assembly 110 to the site of the aneurysm 105, pushed to deploy the embolic coil 160 into the sac 106, and to be reconnected to the gripper assembly 120 as discussed herein.

Figure 11A:
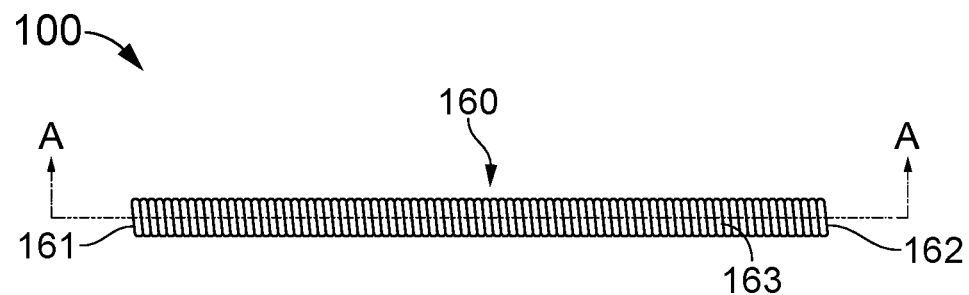
FIGS. 11A, 11B and 11C, taken along lines C-C of FIG. 11B, illustrate schematic side and cross-sectional views of a coil.
Figure 11B:
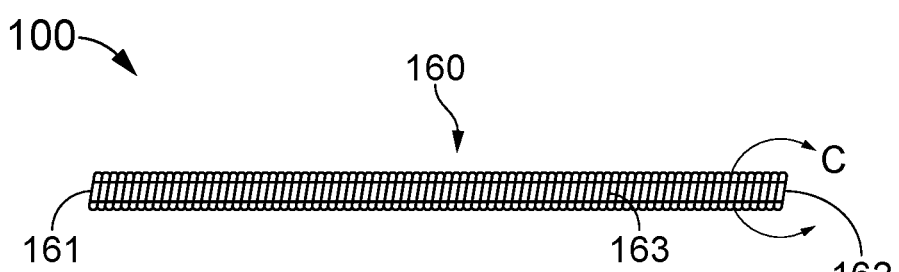
Figure 11C:
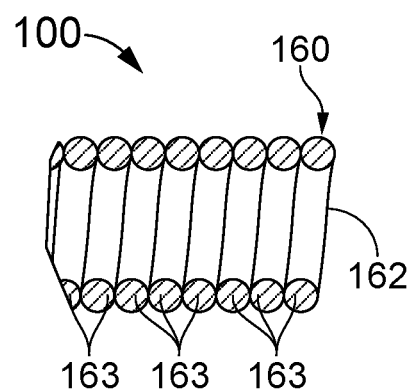

Referring to FIGS. 4, 11A, 11B and 11C, the embolic coil 160 comprises a micro coil that is initially straight along its length, as shown in FIGS. 11A-11C. The embolic coil 160 has a proximal end 161 and distal end 162 and folds into an end-to-end length of primary winding 163. In the straight configuration, the embolic coil 160 is in the form of a wire wrapped in a tight helical fashion about a straight, central longitudinal axis, similar to a coil spring. As described herein, the embolic coil 160 is formed of a shape memory alloy such as a bioalloy, NiTi or a platinum group alloy. The delivery assembly 110 utilizes the catheter 101 to deliver the small diameter embolic coil 160 to the site, the embolic coil 160 is pushed and coiled into the interior sac 106 of the aneurysm.

According to an embodiment of the present invention, the embolic coils 160 are configured to have special properties of a self-adaptive floating diameter that causes the embolic coil 160 to uncoil and frame into the particular shape and diameter of the aneurism sac 106, which is an improvement over the prior art as each of the aneurysm sac 106 is a different diameter and/or shape. The special properties are due to a combination of the structure and predetermined shape 167 and other factors. The ability of the embolic coil 160 to self-adapt to the diameter of the aneurism sac 106 allows the first inserted embolic coil 160 to fill and stabilize to the actual wall shape or diameter of the aneurysm sac 106 thereby creating a stabilizing structure or scaffold. Subsequently inserted embolic coil(s) 160 fill the inner volume of the framing structure created by the first inserted embolic coil 160 causing blood to coagulate and form thrombus which fills the aneurysm cavity, thereby preventing the rupture of the aneurysm and the subsequent bleed. In another example, as shown in FIGS. 7A and 7B, a mandrel 180 is shown that is utilized to fabricate a predetermined shape 167 of the embolic coil 160 according to an embodiment of the present invention.

As is illustrated in FIGS. 7-10, from different perspectives, an embolic coil 160 manufactured on the mandrel 180 (FIG. 6A) results in the embolic coil 160 having special properties of a self-adaptive floating diameter that causes the embolic coil 160 to uncoil and frame into the particular shape and diameter of the aneurism sac 106. In FIG. 7, the embolic coil 160 is in a relaxed, low-energy state as would result in the patient's body or at air temperature. The embolic coil 160 is represents an ordinal 169 arrangement of the predetermined shape 167 comprising a diameter formed of primary 177 and secondary 178 loops. Accordingly, the embolic coil 160 advantageously is of the predetermined shape 167 of primary loop 177, secondary loop 178 and filler loop 179 between the proximal curled end 175 and distal G-loop end 176. The predetermined shape 167 is selected from the set of primary 164, secondary 166, tertiary 168 and/or ordinal 169 arrangements to create the specific properties conforming to a diameter of any aneurysm sac. For example, the embolic coil 160 wants to float to a shape and/or a diameter of an inner surface of the aneurysm sac 106, which permits the self-adaptive floating diameter coil 160 to be used efficiently for a range of aneurysm sac(s) that is also not available in the art, e.g. for a diameter range of 4 mm to 6 mm; 5 mm to 7 mm, and 6 mm to 9 mm.

Referring to FIG. 10, a side view shows the distal curled end 176 that is finished so as not to create any tissue damage in the patient's body. A proximal closed end 175 is formed in a proximal closed end that also is finished so as not to create any tissue damage in the patient's body. In some versions, an atraumatic tip 171 as described above is secured to the distal end 176. The orthogonally looped proximal end 161, T-bit 172 or curled proximal end 175 is useful for insertion, reconnecting and/or repositioning the embolic coil 160 with the opening 124 and recess 125 combining to grab the proximal end using the jaw(s) 122, 123 of the gripper assembly 120 as is illustrated in FIGS. 1B, 19A, 20A-20C of the delivery assembly 110 according to embodiments of the present invention. Accordingly, the orthogonally looped proximal end 161, T-bit 172 or curled proximal end 175 advantageously provides a connection for the jaw 122, 123 movements orthogonal to the plane of the embolic coil 160 primary winding 163 so that the jaw(s) 122, 123 do not exert or impart any force, or an ultra low force, to the embolic coil 160 when disengaging and/or disconnecting the connection to the embolic coil 160.

Figure 9:
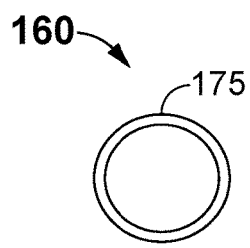
FIG. 9 illustrates an end view of a coil of FIG. 8

Referring to FIG. 9, an end view shows the distal curled end 175; however, for sake of clarity, the pattern is selected from one of the predetermined shapes 167 of the set of primary 164, secondary 166, tertiary 168 and/or ordinal 169 arrangements to achieve specific properties conforming to a diameter of an aneurysm thereby taking the shape of the aneurysm using a method and delivery assembly that can be used to insert, retract, reconnect, and rapidly disconnect from the embolic coil, and such end view may not be connected in a 360 degree loop along the length of the embolic coil 160.

According to specific properties of the embolic coil 160 delivery system and method of the present invention, the void is filled effectively and efficiently requiring less time of the: surgeon, facility used during the embolization procedure, and patient. Thus, an improved time of embolization procedure is realized by the medical therapeutic embolic device, system and method for an embolization procedure 100 that reduces patient risks and overall costs. Moreover, there also is a significant reduction in the number of embolic coils 160 used—whether primary or secondary coils, framing or filling—and with less required materials there is a further reduction in material costs of the embolization procedure. As a result, the device, system and method 100 advantageously reduces time, costs, and risks to the patient which is an improvement over the prior art.

Referring to FIGS. 1A, 1B, 4, 5A-5B, 15A, 15B, 16A, 16B, 17A, 17B, 18A, and 18B, the gripper assembly 120 is configured to hold the orthogonally looped proximal end 161 or curled proximal end 175 of the embolic coil 160, or the T-pin 172 of the coil assembly 170, and to impart push-pull forces to advance or withdraw the embolic coil 160. The gripper assembly 120 comprises one or more distal jaw(s) 122, 123, which can be further designated lower jaw 122 and upper jaw 123, that apply a force to securely hold the orthogonally looped proximal end 161 of the embolic coil 160, as is shown in FIGS. 15A and 15B, or element 175 and/or 177 in FIGS. 7-10, or the T-pin 172 of the coil assembly 170 in the recess 125 of the jaws 122, 123 as shown in FIGS. 1A-1D, 2, FIGS. 17A, 17B and 18A, 18B, and as is illustrated in FIGS. 19A, 20A-20C. The gripper assembly 120 is configured to provide movement that is orthogonal to the plane of the orthogonally looped proximal end 161 of the embolic coil 160 and orthogonal to topological primary winding 163 or looping of the embolic coil 160.

In operation, as illustrated in FIGS. 1A-1B, 5A-5B, 17A, 17B, 18A, and 18B, the gripper assembly 120 is configured to hold the embolic coil 160 a loop interlinked with another loop. Either jaw 122 or jaws 122,123, or mechanical jaw 127, are configured to receive the orthogonally looped proximal end 161, T-bit 172, or curled proximal end 175 of the embolic coil 160 in the recess 125 of the jaws 122, 123 or 127. With the orthogonally looped proximal end 161, T-bit 172, or curled proximal end 175 of the embolic coil 160 positioned in the recess 125, and with the jaws 122, 123, or alternatively mechanical jaw 127 and lower jaw portion 128, in the closed position, the jaws 122, 123 hold the embolic coil 160 so the jaws 122, 123 can impart push-pull forces on the embolic coil 160 to advance or withdraw the embolic coil 160. Each jaw-has an opening 124 and hinge 126 point to locate movement of the jaws 122, 123 or both orthogonal to the plane of the orthogonally looped proximal end 161 and orthogonal to the plane of the primary winding 163 of the embolic coil 160. In the embodiment of FIGS. 15A and 15B, mechanical jaw 127 has rotational motion around pivot 129. According to a feature of the present invention, the jaws 122, 123 are configured so the jaw movement does not exert any force on the embolic coil 160 when disengaging, which is a special property of the gripper assembly 120 of the delivery system 110, resulting in that the embolic coil 160 is not moved, nor damaged. Moreover, within the limitations of the imaging system, typically fluoroscope, the catheter 101 and jaws 122, 123 are visible and can be repositioned to again engage the coil by actuating the jaw 122, or jaw 123, or both, between open and closed positions as necessary.

Figure 12A:
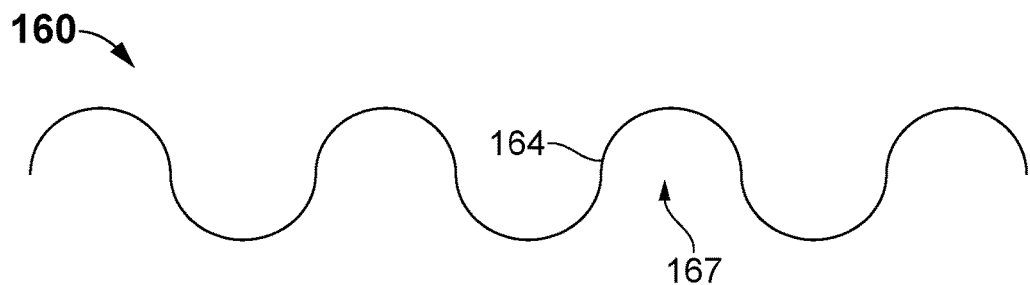
FIGS. 12A, 12B, and 12C illustrate schematic side views of a set of arcuate curvatures, semi-circle-like shapes, alternating between larger and smaller radius, in accordance with an embodiment of the present invention.
Figure 12B:
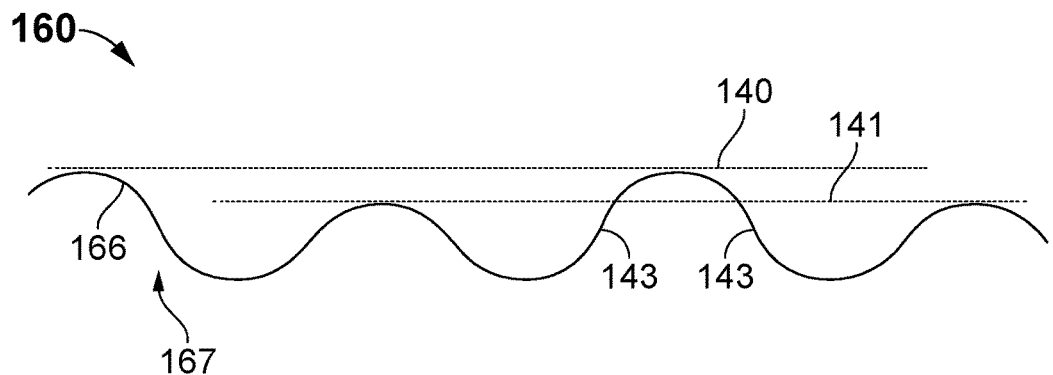
Figure 12C:
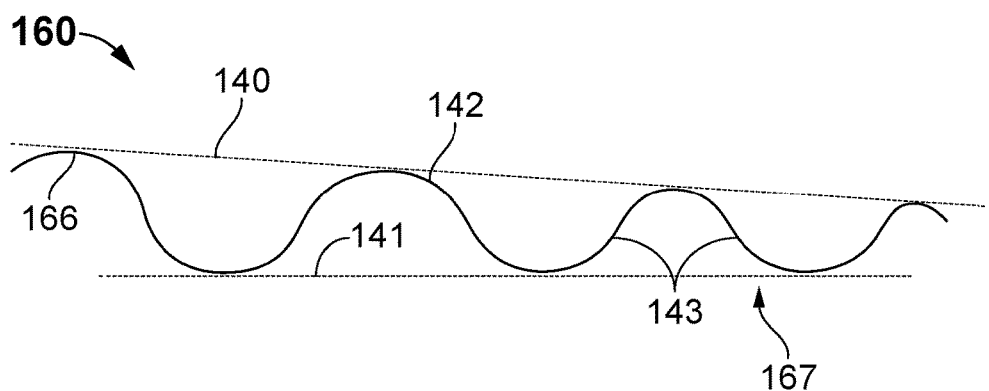
Figure 14A:
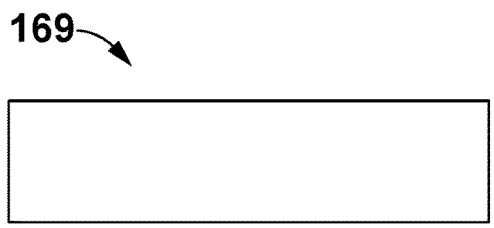
FIGS. 14A, 14B, 14C, 14D, 14E, 14F, 14G, 14H, 14I, and 14J illustrate schematic views of ordinal arrangements in accordance with an alternative embodiment of the present invention.
Figure 14B:
Figure 14C:
Figure 14D:
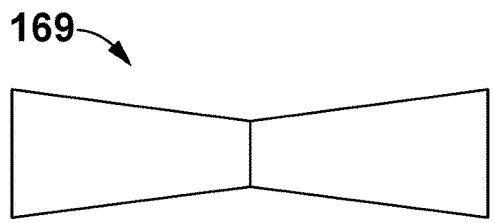
Figure 14E:
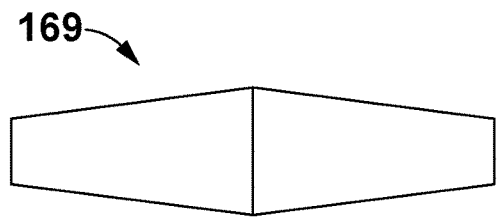
Figure 14F:
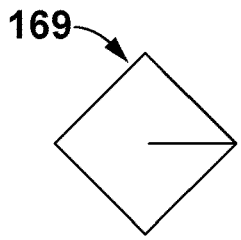
Figure 14G:
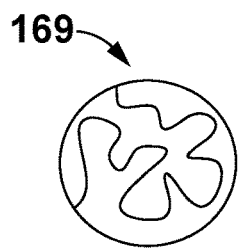
Figure 14H:
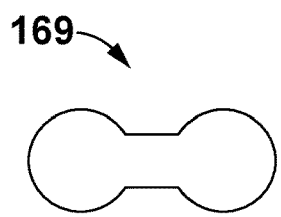
Figure 14I:
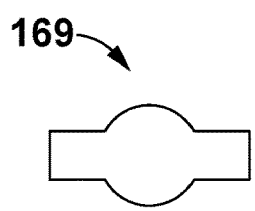
Figure 14J:
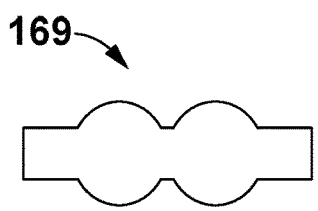

FIGS. 12A, 12B, and 12C illustrate curvatures of the embolic coil 160, which is configured from a wire with a proximal end 161, and a distal end 162 that can be arranged or coiled into a primary winding 163 having a general length and dimension to fit within a catheter 101 of the delivery assembly 110. According to the present invention, a primary coil 164 is configured with a set of arcuate curves or curvatures 165, for example, a series of curvatures, such as S-turns, wave forms or semi-circled shaped turns to form a secondary coil 166 arrangement and an extended length as shown to FIG. 12A. The set of arcuate curves or curvatures 165 is of a predetermined shape 167 whereby a portion of each of the upper crests may or may not be coplanar with respect to one another. For alternating curves in the secondary coil arrangement, these portions of the upper crests are spaced along a substantially straight line. The secondary coil provides additional structure and filling for the aneurysm sac 106.

The predetermined shape 167 includes one or more of the primary 164, secondary 166, tertiary 168 and/or ordinal 169 coil arrangements. A deployed coil 160 within an embolism would then self-curl roughly defining the surface of a sphere. Because the primary 164, secondary 166, tertiary 168 and ordinal 169 coil arrangements can flex. i.e., the embolic coil arrangements may be extended or compressed, the overall geometry of the device is highly flexible, with varied loops spans and can conform to a wide variation in aneurysm size, and particularly, to the size of the neck defining the opening of the aneurysm. As shown in the FIG. 12A, two adjacent curves in the secondary coil arrangement form one semi-circle, and because the device includes a plurality of semi-circles, a semi-circular trajectory path amplitude difference is formed by the embolic coil arrangements. The semi-circular trajectory path amplitude difference may result in the device having a c-shape or the device may be considered to be a cylinder or barrel defining an opening along its side as shown in FIGS. 13B and 13D. Each semi-circle may define a radius different from adjacent semi-circles, as is shown in FIG. 12B. As a result, the device may define a cone-like shape with semi-circles of progressively smaller radii, as is shown in FIG. 12C.

Referring to FIG. 12B, according to an embodiment of the present invention, the secondary coil 166 arrangement forms a series of semi-circles like shapes. Each semi-circle-like shape includes an upper portion defined by a convex acute portion upper datum plane 140 and a lower datum plane 141 defined by the broken edges. The upper datum plane 140 includes three curve segments, a top of curve segment 142 and two side of curve segments 143. Each semi-circle-like shape defines a semi-circle about the longitudinal axis of the secondary configuration of the device. The top segment of the upper datum plane 140 and the lower datum plane (e.g. the broken edges) 141 curve towards one another around the longitudinal axis via the side segments 143 of the top curve segment 142. Returning to the secondary coil arrangement, the successive curves in the secondary coil arrangement define a semi-circular channel.

As illustrated in FIGS. 13A-13D a tertiary 168 is described for the predetermined shape 167 according to another embodiment of the present invention. As is illustrated in FIG. 13A, a tertiary 168 (and secondary and tertiary $3^{rd}$ sinusoidal wave) arrangement set of shapes are made up of the primary coil 164 with semicircular shapes either uniform in geometry or random that follow the trajectory of the secondary coil 166 in accordance with an alternative embodiment of the present invention. The tertiary 168 arrangement of the primary coil 164 follows a semi-circular trajectory (dotted) and the secondary coil 166 (solid) follows along a tertiary path 157 of the trajectory of the primary coil 164. As above, the primary coil 164 arrangement is defined by curvatures extending along a length of the embolic coil 160 between the proximal end 161 and a distal end 162. As is illustrated in FIG. 13A, the secondary coil 166 arrangement is defined by a second set of waveform-like curves, which waveforms can be uniform or random in height of the peak and depth of the trough, and extend along the trajectory (dotted-line) of the primary coil 164. The tertiary 168 arrangement is comprised of the primary coil 164 with semicircular shapes either uniform in geometry or random that follow the trajectory of the secondary coil 166. For example, a tertiary 168 set of shapes for coil 160 is made up of the primary coil 164 with semicircular shapes either uniform in geometry or random in height of the peak and depth of the trough along the tertiary 168 arrangement that follow the trajectory of the secondary coil 166. As shown in FIGS. 13B, 13C and 13D, the tertiary 168 arrangement is illustrated and as viewing the embolic coil 160 from the perspective of the longitudinal as an axial point, the offset a circular arc of greater than about 270 degrees but less than 360 degrees, i.e., the circle is not closed, it is an offset. Viewing the longitudinal axis as a longitudinal line, the semi-circles are offset and are each defined by adjacent curves extending along the length of the device, as shown in FIG. 13C. The crest portions of the curves in the secondary coil arrangement define the open ends of the semi-circle, as shown in FIGS. 13B and 13D. The trough portions of the curves form a link between the successive semi-circle portions and define the closed portion of the semi-circle FIG. 13C.

Referring to FIGS. 14A, 14B, 14C, and 14I, the ordinal 169 arrangement of the embolic coil 160 is described in accordance with an alternative embodiments of the present invention. Referring to FIGS. 14A through 14I, the ordinal plane of the coil 160 follows a path about a circular, cylindrical, conical, oscillating, spherical or triangular form along its longitudinal axis. an arrangement of waveform-like curves extending along a length of the device between a proximal end and a distal end; a plurality of semi-circle or semi-circular like shapes; where each of the semi-circle-like shapes are defined by a plurality of the waveform-like curves and comprises an upper portion comprising an acute-shape and a lower portion with opposing outwardly turned first and second sides, the semi-circle-like shapes joined by the outwardly turned sides of adjacent semi-circle-like shapes, where the upper and lower portions of the semi-circle-like shapes extend towards one another without overlapping to define a series of offset semi-circles arranged about a longitudinal axis of the secondary configuration of the device between the proximal and a distal end.

Referring to FIGS. 15 through 18, a gripper assembly 120 for the primary disconnecting of the coil 160 is described in accordance with various embodiments of the present invention. The gripper assembly 120 may be formed electromechanically detach the embolic coil 160 from the delivery assembly 120 according to an embodiment of the present invention as shown in FIGS. 17A, 17B, 18A, and 18B. The gripper assembly 120 may be formed as a mechanical disconnect to detach the embolic coil 160 from the delivery assembly 120 according to another embodiment of the present invention, as shown in FIGS. 15A and 15B. Similarly, the gripper assembly 120 may be a mechanical disconnect with electrical assist to detach the embolic coil 160 from the delivery assembly 120 according to yet another alternative embodiment of the present invention, as shown in FIGS. 15A, 15B, 16A, and 16B. In each embodiment, the gripper assembly 120 is configured to secure to, hold, detach and re-connect to a loop 163 of the embolic coil 160, which loop of the embolic coil 160 can be located anywhere yet preferably the loop is on a proximal end 161.

The embolic coil 160 may be formed with an orthogonally looped proximal end 161, T-bit 172, or curled proximal end 175 or other geometric shape protruding from the primary windings 163 and preferably proximal end 161, thereby providing a means to grasp the embolic coil 160 and to hold with the gripper assembly 120. The grip may be formed from a pair of distal jaws 122, 123 that engage each other after receiving the orthogonally looped proximal end 161, T-bit 172, or curled proximal end 175 of the embolic coil 160 in the recess 125 of the jaws 122, 123. The jaw 122, 123 elements hold the embolic coil 160 so the pusher (formed by tube 111 and intermediate coil 114) can exert push-pull forces to advance or withdraw the coil.

In an alternative embodiment of a mechanical gripper assembly 120, as is illustrated in FIGS. 15A and 15B, the gripper assembly 120 may be formed with a mechanical jaw 127, a lower jaw portion 128 having a slight bend to cooperate with the arc of the mechanical jaw 127 to form a recess 125 to secure an orthogonally looped proximal end 161 of the embolic coil 160. A pull wire 131 can be utilized so as to move the mechanical jaw 127 between an open and closed position as a primary disconnect in accordance with an embodiment of the present invention. The pull wire 131 would be operable to translate independently relative to tube 111 and intermediate coil 114 to actuate mechanical jaw 127. It should also be understood that wires 116, 118 may be omitted in versions of gripper assembly 120 that utilize a translating pull wire 131 and pivoting mechanical jaw 127 to selectively hold and release the embolic coil 160. In FIG. 15A, when the embolic coil 160 is to be disconnected, a mechanical element of the pull wire 131 is used to force the mechanical jaw 127 to open rotating around pivot 129 to an open position, for example, using a pull wire with return spring. Alternatively, a shape-memory alloy mechanical disconnect with electrical assist can be utilized as discussed in FIG. 16A. At the point of jaw capture of the embolic coil 160, when it is to be connected, the movement around the pivot 129 of the mechanical jaw 127 is orthogonal to the plane of the orthogonally looped proximal end 161 of the embolic coil 160, as shown in FIG. 15B as well as curled proximal end 175, or T-pin 172.

Figure 16A:
FIGS. 16A and 16B illustrate schematic views of a memory shape alloy for a pusher wire in accordance with an embodiment of the present invention.
Figure 16B:

Referring to FIGS. 16A and 16B, NiTiNOL wires may be used for the push/pull wire 131, whereby the zigzag wire form of the cool NiTi wire 132 (FIG. 16A) is energized and/or warm; and the flat form of the warm NiTi wire 133 (FIG. 16B) is non-energized or cold (not-heated, non-energized). Referring to FIG. 16A, the NiTi cool wire 132 is functioning to disconnect the orthogonally looped proximal end 161 of the coil 160 from the arc of the mechanical jaw 127 and the lower jaw portion 128. In particular, the mechanical jaw 127 is moved to the opened position (FIG. 15A) by energizing the pull wire 131, changing the shape-memory alloy from the tightly zigzagged shape of the cool NiTi wire 132 (FIG. 16A) to the warm NiTi wire 133, to bias to the open position around pivot 129. The mechanical jaw 127 closes on the orthogonally looped proximal end 161 by de-energizing, thereby allowing the pull wire 131 to regain its relaxed flat shape when cool as shown in FIGS. 15B and 16B, when the alloy of the 133 is cold so as to take the form in a relaxed flat shape. Accordingly, the gripper assembly 120 functions to hold and release the embolic coil 160 using the push/pull wire 131 advantageously using the shape-memory alloy to contract the pull wire 131 when warm and to elongate the warm wire 133 when relaxed.

For example, in operation according to the embodiments of FIGS. 15A, 15B, 16A and 16B, in an embolization procedure the embolic coil 160 can be delivered by the push/pull wire 131 where the mechanical jaw 127 is moved to the open position when the push/pull wire 131 is warmed as shown in FIG. 16A, or returned to the closed position when cooled as shown in FIG. 16B in the flat shape configuration. In a similar manner, an electronic circuit can be formed to warm and cool the NiTi wire of the gripper assembly 120. For example, a core wire 116 and ground wire can impart current to the pull wire 131 so as to create the shape of the cool NiTi wire 132 and warm NiTi wire 133. In this way, the gripper assembly 120 is configured to release the embolic coil 160 by passing an electric current down the pull wire 131 in order, for example, to warm or raise the temperature of the NiTi or other shape-memory alloy, thereby causing the shape-memory alloy to change form—taking a tightly zigzagged or relaxed flat shape (shown in FIGS. 16A and 16B)—resulting in moving the mechanical jaw 127 to an open position and releasing the primary winding 163 of the embolic coil 160. Upon removing the current, heating will stop, and the pull wire will cool, thereby allowing the mechanical jaw 127 to conform back to the natural form—the relaxed flat shape—thus recapturing the proximal end of the primary winding 163 embolic coil 160, as is illustrated in FIGS. 15B and 16B.

As is illustrated in FIGS. 17A and 17B, the gripper assembly 120 is configured with a tip 121, lower jaw 122, upper jaw 123, and a opening 124 in the material with one or more circular recess 125 along the opening 124 leading to a hinge 126. One or more circular recess 125 is disposed in jaws 122, 123 (or alternatively the tip 121 and jaw 122 shown in FIG. 18A, 18B), and the recess 125 is configured to capture the orthogonally looped proximal end 161 or curled proximal end 175 of the embolic coil 160, or alternatively the T-pin or bit 172 of the coil assembly 170. FIGS. 17A and 17B illustrate an open position and a closed position, respectively for the jaws 122, 123 having such two-way movement at hinge 126. The movement is actuated by the gripper assembly 120, e.g. by heating the electrically conductive tip connector 119 by the current applied by core and ground wires 116, 118, respectively, as described in accordance with an embodiment of the present invention.

According to FIG. 17A, the lower and upper jaws 122 and 123, respectively, are shown in the closed position, and in FIG. 17B, the jaws 122, 123 open on both sides by two-way pivot movement at hinge 126 to an open position. The tip 121 is formed from a shape-memory alloy such as NiTi or NiTiNOL configured to move to an open position when an electrical current is applied, e.g. opening by heating the core and ground wires 116, 118 that are in conductive engagement through tip connector 119, as shown in FIG. 17B. The jaws 122, 123 are configured to return to the closed position after electrical current is halted, as shown in FIG. 17A. As a result, electrical current, or heat operates, the gripper assembly 120 so as to connect or disconnect the embolic coil from the jaws 122, 123, thereby advantageously exerting little or no force on the embolic coil 160 to disconnect. Upon opening the jaws 122, 123 the embolic coil 160 may be released without movement or damages thereto. Rather, the opened jaws 122, 123 may be moved away from the orthogonally looped proximal end 161, curled proximal end 175, or T-pin 172, and then be retracted proximally relative to the embolic coil 160, to fully disengage the delivery assembly 110 from the embolic coil 160.

Because the jaws 122, 123 may be opened and closed, the jaws 122, 123 will remain open as long as electrical current is applied, or toggled electrically so as to re-opened and closed used to re-engage the coil, at which point the drive assembly 110 may exert push-pull forces on the embolic coil 160 to reposition it in the aneurysm sac 106. As discussed in regards to FIGS. 15 and 16, the use of shape-memory alloys can be used for the gripper assembly 120 and jaw 122, 123, e.g. NiTiNOL. For example, the lower jaw 122 can be actuated by electrical current to release the coil 160 as shown in FIG. 18B, and the jaw 122 will return to its closed position, shown in FIG. 18A, after electrical current is halted. Repositioning of the embolic coil can be accomplished by relocating the jaw and reengaging the embolic coil by actuation of the jaw. The jaws may be fabricated from radiopaque materials to aid in the position of the tip 121 and the jaws 122, 123 relative to the embolic coil 160 for reattachment. The radiopaque nature of the jaws 122, 123 can also assist in the initial positioning of the embolic coil 160 at the site of the aneurysm sac 106. The embolic coil 160 also is formed of radiopaque material allowing both the delivery assembly 110 and coil 160 to be visible under fluoroscopy or other imaging devices. In this manner, the tip 121 can have a single jaw 122 movement as is illustrated in FIGS. 18A and 18B, i.e. a gripper assembly 120 jaw 122 having a one-way movement hinge 126 as an alternative embodiment of the present invention. According to FIG. 18A, a disconnect by lower jaw 122 having a one-way movement hinge 126 can be biased in the closed position in a non-electrically energized state. According to FIG. 18B, the disconnect jaw opens on one side of the distal end using the one-way movement pivoting at the hinge 126 to an open position in an electrically energized state.

Moreover, shape-memory alloys can be used to extend the tip 121 from the body of the catheter 101 by similar operation of an electrically energized state, whereby the tip 121 slides out of the catheter 101, thereby extending the jaw(s) 122, 123 relative to the catheter 101, and is useful for the specific operation of a rapid disconnect. Using a shape memory alloy, for example, the primary disconnect jaw 122 of FIG. 18A will be connected to a push/pull wire 131. The rapid disconnect of the embolic coil 160 from jaw 122 may be actuated by applying electrical current to release the embolic coil 160. Halting electrical current to the jaw 122, the jaws 122, 123 close and the user can then return the tip 121 into the catheter 101, as is shown in FIG. 19C, thereby reducing any trauma upon resection.

Referring to FIGS. 19A, 19B, and 19C, the configured process that may be used to deliver and release the embolic coil 160 to the proper site 105 in the patient's body in an embolization procedure is described in accordance with an embodiment of the present invention. Referring to FIG. 19A, using a delivery assembly 110 an embolic coil 160 is positioned at the proper site 105 in the patient's body adjacent the aneurysm. Referring to FIG. 19B, advancing the pusher (formed by tube 111 and intermediate coil 114) pushes the embolic coil 160 out into the aneurysm sac 106. One or more coils 160 can be pushed out into the aneurysm sac 106. Referring to FIG. 19C, the coil 160 is released and deployed in the aneurysm sac 106 in an embolization procedure and the delivery assembly 110 is retracted from the site in the patient's body adjacent the aneurysm.

Figure 20A:
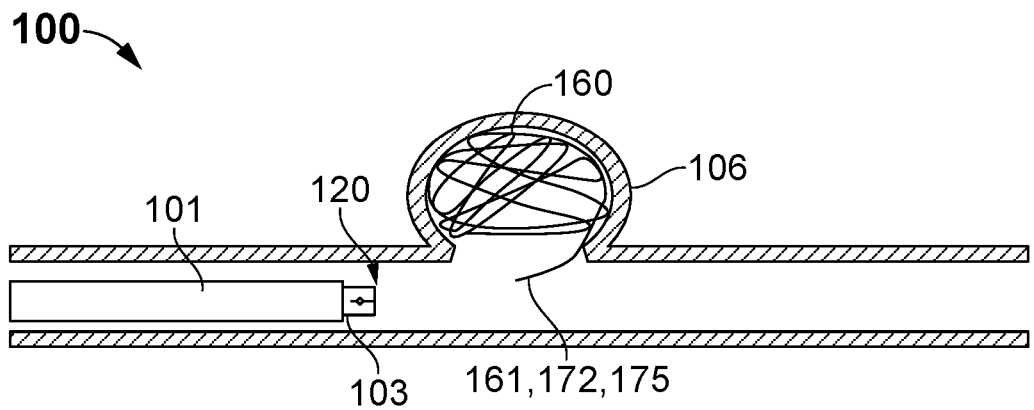
FIGS. 20A, 20B and 20C illustrate schematic views of c using a delivery system in an embolization procedure reconnecting an embolic coil and then deploying into the sac in accordance with an embodiment of the present invention.
Figure 20B:
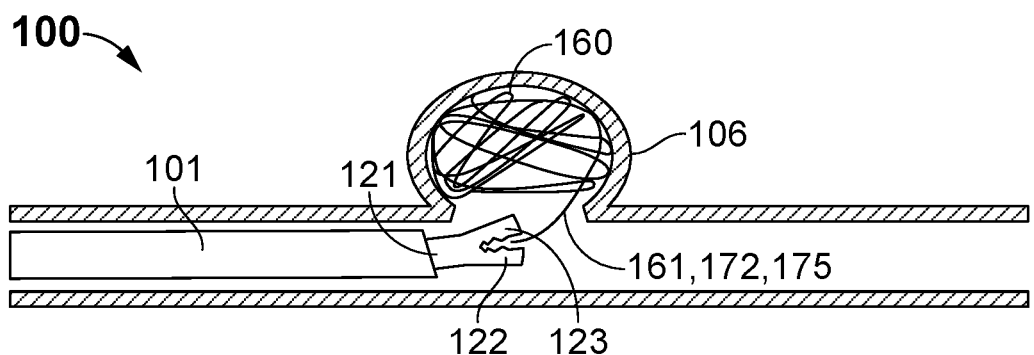
Figure 20C:
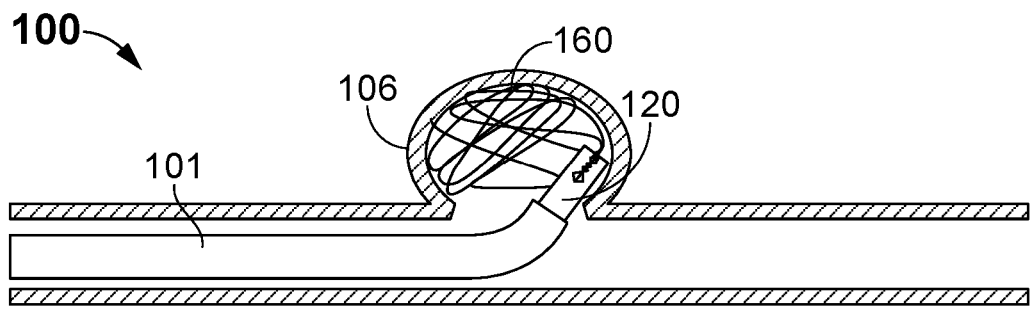

As illustrated in FIGS. 20A, 20B and 20C, the recapture of the embolic coil 160 in an embolization procedure is described in accordance with an embodiment of the present invention. Sometimes in an embolization procedure, the embolic coil 160 moves due to mechanical movement in the disconnect or other factors such as, for example, leaving a tail of the orthogonally looped proximal end 161, curled proximal end 175 or T-pin 172 of the embolic coil 160 hanging in the lumen of the artery where it can cause turbulence, adverse events and other health dangers to the patient. In conventional mechanical disconnect connections, the tail would be pushed back by the head of the catheter or by trying to tangle and reinsert by add another coil. In conventional systems once released from the latch, the embolic coil 160 is free and no more control can be exerted over the coil. Referring to FIG. 20A, the orthogonally looped proximal end 161, curled proximal end 175 or T-pin 172 of the embolic coil 160 is shown extending hanging in the lumen of the artery. Referring to FIG. 20A, using a delivery assembly 110 the jaws 122, 123 are positioned at the proper site in the patient's body adjacent the tail of a coil 160. The gripper assembly 120 is energized to open the jaws 122, 123. Referring to FIG. 20B, the jaws 122, 123 of the gripper assembly 120 are opened and arranged around the orthogonally looped proximal end 161, curled proximal end 175 or T-pin 172, then closed by de-energizing the gripper assembly 120, closing the jaws 122, 123 on the orthogonally looped proximal end 161, curled proximal end 175 or T-pin 172 the embolic coil 160, thereby connecting to the embolic coil 160 again. The delivery assembly 110 is advanced to push the embolic coil 160 into the aneurysm sac 106 as shown in FIG. 20C. Referring to FIG. 19B, the jaws 122, 123 of the gripper assembly 120 are opened to release from coil 160 deployed in the aneurysm sac 106. The delivery assembly 110 is retracted from the site in the patient's body adjacent the aneurysm, as shown in FIG. 19C.

As is illustrated in FIGS. 21A, 21B, 21C and 21D, a balloon assembly 130 may be configured to deliver and release the embolic coil 160 to the proper site in the patient's body. The balloon assembly 130 can be connected to the shaft 134 and to be made operable to expand, inflate or balloon, for example, upon application of current or heat via the wires 116, 118 to change the shape of the balloon. In operation, the embolic coil 160 an moved, positioned, reconnected and released utilizing a balloon to deploy the embolic coil 160 from a catheter 101 in accordance with an embodiment of the present invention. Accordingly, a micro inflatable balloon 130 can be attached to a distal end of shaft 134.

Figure 21A:
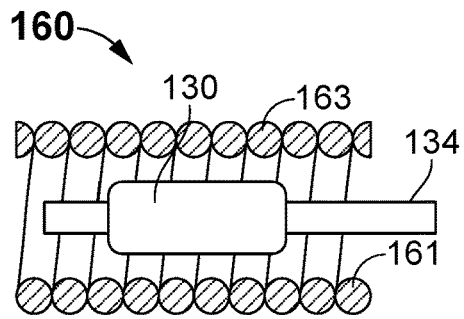
FIGS. 21A, 21B, 21C, and 21D illustrate schematic views of a delivery assembly featuring a balloon to deploy a coil with disconnect and/or reconnect properties in accordance with an alternative embodiment of the present invention.
Figure 21B:
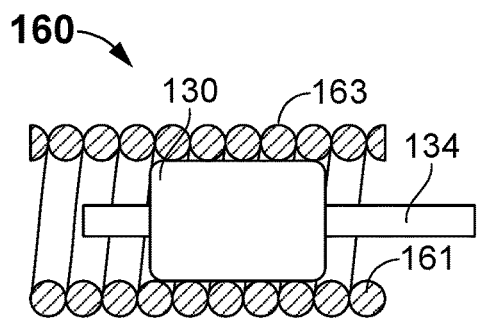
Figure 21C:
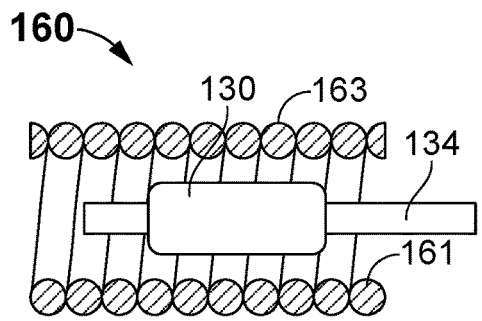
Figure 21D:
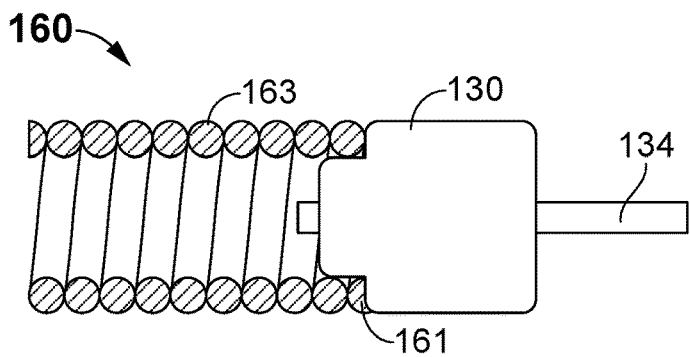

The balloon 130 can be loaded into an interior portion of the embolic coil 160, as shown in FIG. 21A, and inflated to engage with primary winding 163, as shown in FIG. 21B. Referring to FIG. 21B, in the inflated state the balloon 130 is in positive engagement with the interior surface of one or more of the primary winding 163 of the embolic coil 160. Once in positive engagement, fine positioning can be accomplished to move the embolic coil 160. Referring to FIG. 21D, the balloon 130 can also be inflated at the proximal end 161 of the embolic coil 160 to insert into the aneurysm sac 106. For example, the balloon 130 engages both the proximal end 161 of the primary winding 163 of the embolic coil 160 and the lumen or an interior surface of the catheter 101, whereby advancing the shaft 134 pushes the embolic coil 160 into the aneurysm sac 106 advantageously from the distal end 103 of the catheter 101. In some versions of this embodiment, the proximal end 161 of embolic coil 160 is not orthogonally looped. As is illustrated in FIG. 21C, after the embolic coil 160 has been placed in the proper site, the balloon 130 can be deflated for removal such as, for example, pulling the balloon 130 back into the catheter 101 and retracting from the site, as is shown in FIG. 19C.

The device, system and method 100 has numerous features and operability including (1) a zero force disconnect gripper assembly 120 from jaw movement orthogonal to the plane of the orthogonally looped proximal end 161, curled end 175, or T-bit 172 of the embolic coil 160 so that the jaw(s) 122, 123 or balloon 130 do not exert or impart any force, or an ultra low force, to the embolic coil 160 when disengaging and/or disconnecting the connection to the coil; (2) an ability to re-connect with the gripper assembly 120 utilizing mechanical or electro-mechanical operation. Moreover, the embolic coil 160 of the system 100 is configured advantageously with (1) a low deployment force; (2) a material selection and construction where one coil size can be used for multiple aneurysm sizes; and (3) a unique self-adapting coiling shape that requires less coils in the treatment or embolization procedure, thereby saving time, cost and lowering risks to the patient.

While certain configurations of structures have been illustrated for the purposes of presenting the basic structures of the present invention, one of ordinary skill in the art will appreciate that other variations are possible which would still fall within the scope of the appended claims. For example, the gripper assembly 120 can be configured to capture and recapture with magnetic properties or utilizing the phase change of the shape-memory metal alloy. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A vaso-occlusive device, consisting of:
   a self-adaptive floating diameter member, consisting of:
   a distal end with an anchoring loop for anchoring said self-adaptive floating diameter member to an inner surface of a vessel at a site of an embolization procedure;
   a proximal end with a proximal loop for detaching from a gripper assembly adapted to deliver to said site of said embolization procedure;
   a primary coil arrangement configured with a plurality of primary omega curves extending along a length of said self-adaptive floating diameter member between said proximal end and said distal end;
   a secondary coil arrangement configured with a plurality of secondary omega curves extending along a trajectory along said length of said self-adaptive floating diameter member between said proximal end and said distal end, said plurality of secondary omega curves configured in an arcuate curvature comprising an upper crest portion and a lower trough portion following said trajectory of said plurality of primary omega curves about a longitudinal axis of said self-adaptive floating diameter member between said proximal end and said distal end; and
   whereby said primary coil arrangement and said secondary coil arrangement in a relaxed, state in the patient's body substantially assume a shape of said inner surface of said vessel at said site of said embolization procedure.

2. The vaso-occlusive device of claim 1, wherein said self-adaptive floating diameter member is configured for a range of diameters of said vessel and/or an aneurysm sac.

3. The vaso-occlusive device of claim 1, wherein said proximal loop is configured to extend orthogonal to a plane of said gripper assembly and is adapted for re-connection to said gripper assembly.

4. The vaso-occlusive device of claim 1, wherein said self-adaptive floating diameter member comprises a coil.

5. The vaso-occlusive device of claim 1, wherein said self-adaptive floating diameter member is configured to disconnect said proximal end from said gripper assembly with a zero force disconnect.

6. The vaso-occlusive device of claim 1, wherein said arcuate curvatures can be uniform or random in height of said upper crest portion and said lower trough portion along said trajectory of said self-adaptive floating diameter member between said proximal end and said distal end.

7. The vaso-occlusive device of claim 1, wherein said proximal end of said self-adaptive floating diameter member is configured to allow electro-mechanical detachment from said gripper assembly.

8. The vaso-occlusive device of claim 1, wherein said proximal end of said self-adaptive floating diameter member is configured to allow mechanical detachment from said gripper assembly.

9. The vaso-occlusive device of claim 1, wherein said proximal end of said self-adaptive floating diameter member is configured to allow chemical detachment from said gripper delivery assembly.

10. The vaso-occlusive device of claim 1, wherein said proximal end of said self-adaptive floating diameter member is configured to allow thermal detachment from said gripper assembly.

11. The vaso-occlusive device of claim 1, wherein said self-adaptive floating diameter member is formed from a shape-memory alloy.

12. The vaso-occlusive device of claim 1, wherein said self-adaptive floating diameter member is formed from a shape-settable alloy from a group consisting of a biocompatible metal wire, platinum, tungsten, titanium, gold, iridium, palladium, tantalum, and a platinum alloy.

13. The vaso-occlusive device of claim 1, wherein said proximal loop is adjacent said primary coil arrangement for operably coupling to a distal recess in one or more jaws of said gripper assembly.

14. The vaso-occlusive device of claim 1, wherein said proximal loop is adjacent said primary coil arrangement and is adapted for re-connection to said gripper assembly.

15. The vaso-occlusive device of claim 1, wherein a first transition primary omega curve of said plurality of primary omega curves is located adjacent said anchoring loop of said distal end, said transition primary omega curve operably connected to said anchoring loop to float adaptively in a direction of said inner surface adjacent said anchoring loop.

16. The vaso-occlusive device of claim 1, wherein a first transition primary omega curve of said plurality of primary omega curves is located adjacent said anchoring loop of said distal end, said transition primary omega curve operably connected to said anchoring loop to float adaptively in a direction of said inner surface adjacent said anchoring loop for securing and holding said self-adaptive floating diameter member to said inner surface of said vessel.

17. The vaso-occlusive device of claim 1, wherein said plurality of primary omega curves is configured to uncoil and frame into a particular shape and diameter of said inner surface of said vessel.

18. The vaso-occlusive device of claim 1, wherein said primary coil arrangement of said plurality of primary omega curves is configured to conform adaptively at said plurality of primary omega curves into a particular shape and diameter of said inner surface of said vessel.

19. The vaso-occlusive device of claim 1, wherein said primary coil arrangement is formed on a mandrel configured in a cylinder shape so as to provide said plurality of primary omega curves the conform adaptively at said plurality of primary omega curves into a particular shape and diameter of said inner surface of said vessel.

20. The vaso-occlusive device of claim 1, wherein said secondary coil arrangement is configured to uncoil and frame into a particular shape and diameter of said inner surface of said vessel.

21. The vaso-occlusive device of claim 1, wherein said secondary coil arrangement is configured to conform adaptively at said plurality of primary omega curves and frame into a particular shape and diameter of said inner surface of said vessel.

22. The vaso-occlusive device of claim 1, wherein said secondary coil arrangement is formed on a mandrel configured in a cylinder shape so as to provide said plurality of secondary omega curves that conform adaptively at said plurality of secondary omega curves into a particular shape and diameter of said inner surface of said vessel.

23. The vaso-occlusive device of claim 1, wherein said anchoring loop is configured in a G-loop shape.

* * * * *